US012624002B2

(12) United States Patent
Al-Abed et al.

(10) Patent No.: US 12,624,002 B2
(45) Date of Patent: May 12, 2026

(54) DIMERS FOR USE IN SYNTHESIS OF PEPTIDOMIMETICS

(71) Applicant: THE FEINSTEIN INSTITUTES FOR MEDICAL RESEARCH, Manhasset, NY (US)

(72) Inventors: Yousef Al-Abed, Manhasset, NY (US); Ahmad Altiti, Piscataway, NJ (US)

(73) Assignee: THE FEINSTEIN INSTITUTES FOR MEDICAL RESEARCH, Manhasset, NY (US)

( * ) Notice: Subject to any disclaimer, the term of this patent is extended or adjusted under 35 U.S.C. 154(b) by 658 days.

(21) Appl. No.: 17/922,945

(22) PCT Filed: May 7, 2021

(86) PCT No.: PCT/US2021/031246

§ 371 (c)(1),
(2) Date: Nov. 2, 2022

(87) PCT Pub. No.: WO2021/226431

PCT Pub. Date: Nov. 11, 2021

(65) Prior Publication Data

US 2023/0159450 A1 May 25, 2023

Related U.S. Application Data

(60) Provisional application No. 63/021,803, filed on May 8, 2020.

(51) Int. Cl.
*C07C 333/12* (2006.01)
*C07D 207/16* (2006.01)
*C07D 231/04* (2006.01)

(52) U.S. Cl.
CPC .......... *C07C 333/12* (2013.01); *C07D 207/16* (2013.01); *C07D 231/04* (2013.01)

(58) Field of Classification Search
CPC .... C07C 333/12; C07D 207/16; C07D 231/04
See application file for complete search history.

(56) References Cited

U.S. PATENT DOCUMENTS

| | | | |
|---|---|---|---|
| 5,157,123 | A | 10/1992 | Zara et al. |
| 5,202,312 | A | 4/1993 | Matsumoto et al. |
| 5,602,231 | A | 2/1997 | Cotton et al. |
| 5,646,276 | A | 7/1997 | Robl |
| 6,784,293 | B1 | 8/2004 | Wu et al. |
| 8,563,565 | B2 | 10/2013 | Norimine et al. |
| 9,186,371 | B2 | 11/2015 | Taniguchi et al. |
| 10,919,882 | B2 | 2/2021 | Al-Abed et al. |
| 11,414,405 | B2 | 8/2022 | Al-Abed et al. |
| 11,440,881 | B2 | 9/2022 | Al-Abed et al. |
| 11,471,507 | B2 | 10/2022 | Al-Abed et al. |
| 11,471,508 | B2 | 10/2022 | Al-Abed et al. |
| 2006/0281686 | A1 | 12/2006 | Lopez Areiza et al. |
| 2011/0086836 | A1 | 4/2011 | Soeberdt et al. |
| 2018/0344808 | A1 | 12/2018 | Tracey et al. |
| 2019/0055283 | A1 | 2/2019 | Ekici et al. |
| 2020/0354404 | A1 | 11/2020 | Al-Abed |
| 2020/0354418 | A1 | 11/2020 | Al-Abed |
| 2021/0000908 | A1 | 1/2021 | Al-Abed |
| 2022/0306577 | A1 | 9/2022 | Al-Abed et al. |

FOREIGN PATENT DOCUMENTS

| | | | |
|---|---|---|---|
| EP | 2113513 A2 | 11/2009 |
| GB | 826300 | 9/1957 |
| KR | 10-2005-0099732 | 10/2005 |
| KR | 20050099732 A | 10/2005 |
| WO | WO 2016/094899 A2 | 6/2016 |
| WO | WO 2019007383 A1 | 1/2019 |
| WO | WO2019/127607 A1 | 7/2019 |
| WO | WO 2020227592 A1 | 11/2020 |

OTHER PUBLICATIONS

Pare Emily C. et al: "Synthesis of 1,5-diisopropyl substituted 6-oxoverdazyls", Organic & Biomolecular Chemistry, vol. 3, No. 23, Jan. 1, 2005 (Jan. 1, 2005), p. 4258, XP093194141, ISSN: 1477-0520, DOI: 10.1039/b510075e.
Rabong Constantin et al: "NXO beta structure mimicry: an ultra-short turn/hairpin mimic that folds in water", RSC Advances, vol. 4, No. 41, Jan. 1, 2014 (Jan. 1, 2014), pp. 21351-21360, XP093194142, GB ISSN: 2046-2069, DOI: 10.1039/C4RA01210K.
Abo-Oya Nader E. et al: "Benzotriazole-Mediated Synthesis of Aza-peptides: En Route to an Aza-Leuenkephalin Analogue", The Journal of Organic Chemistry, vol. 78, No. 8, Apr. 10, 2013 (Apr. 10, 2013), pp. 3541-3552, XP093194146, United States ISSN: 0022-3263, DOI: 10.1021 /jo302251e.
Zhou Zhou et al: "Synthesis and Structural Characterization of 2:1 [[alpha]/ Aza]-oligomers", European Journal of Organic Chemistry, Wiley-VCH, DE, vol. 2014, No. 34, Oct. 21, 2014 (Oct. 21, 2014), pp. 7643-7650, XP072112427, ISSN: 1434-193X, DOI: 10.1002/ EJOC.201402628.
PubChem AKOS000648614, Modify Date: Feb. 22, 2011.
PubChem 2-(2-(1,3-Dioxoisoindolin-2-yl)acetamido)acetyl chloride, Modify Date: Mar. 31, 2020.
PubChem AC1 MBWCP, Modify Date: Mar. 7, 2011.
Pérez-Picaso L, Olivo HF, Argotte-Ramos R, Rodríguez-Gutiérrez M, Rios MY. Linear and cyclic dipeptides with antimalarial activity. Bioorg Med Chem Lett. Dec. 1, 2012;22(23):7048-51. doi: 10.1016/ j.bmcl.2012.09.094. Epub Oct. 2, 2012. PMID: 23084276.
Supplementary Partial European Search Report EP21800750.8, mailed on Sep. 24, 2024.
Chemical Abstracts Service. STN database. "CAS Registry No. 4976-75-4. CA Index Name: 2-Isoindolineacetic acid, alpha-[2-(methylthio)ethyl]-1,3-dioxo-, 2-carboxyhydrazide, tertbutyl ester, (S)-". Entered STN: Nov. 16, 1984.

(Continued)

*Primary Examiner* — Kamal A Saeed
(74) *Attorney, Agent, or Firm* — Davidson Kappel LLC

(57) ABSTRACT

Dimers for use in synthesis of peptidomimetics are described. Uses of dimers as synthons in synthesis of azapeptides and other peptidomimetics, azapeptides and other peptidomimetics synthesized from the dimers and uses of azapeptides and other peptidomimetics are also described.

19 Claims, No Drawings

(56) References Cited

OTHER PUBLICATIONS

Chemical Abstracts Service. STN database. "CAS Registry No. 32668-16-9. CA Indexname: Glutaramic acid, 2-phthalimido-, 2-carboxyhydrazide tert-butyl ester, L-". Entered STN: Nov. 16, 1984.
Chemical Abstracts Service. STN database. "CAS Registry No. 2896-89-1.CA Index Name: 2-Isoindolineacetic acid, alpha-isobutyl-1,3-dioxo-, 2-carboxyhydrazide, tert-butyl ester." Entered STN: Nov. 16, 1984.
Chemical Abstracts Service. STN database. "CAS Registry No. 1810074-96-4. CA Index Name: Hydrazinecarbothioic acid, 2-[2-(1,3-dihydro-1,3-dioxo-2H-isoindol-2-yl) acetyl]-, potassium salt". Entered STN: Oct. 15, 2015.
Chemical Abstracts Service. STN database. "CAS Registry No. 892151-00-7. CA Index Name: 2H-Isoindole-2-acetic acid, 1,3-dihydro-1,3-dioxo-,2-(ethoxycarbonyl) hydrazide". Entered STN: Jul. 12, 2006.
Chemical Abstracts Service. STN database. "CAS Registry No. 1810074-95-3. CA Index Name: Hydrazinecarbothioic acid, 2-[2-(1,3-dihydro-1,3-dioxo-2H-isoindol-2-yl)acetyl]-". Entered STN: Oct. 15, 2015.
Abbas C, et al. "Original and efficient synthesis of 2:1 [alpha/aza]-oligomer precursors". Tetrahedron Letters. Jul. 15, 2009; 50(28):4158-60.
PubChem-SID-105195820, Modify Date: May 30, 2019, p. 2, figure.
PubChem-SID-405014557, Modify Date: Mar. 31, 2020, p. 2, figure.
PubChem-SID-111355128, Modify Date: Mar. 7, 2011, p. 2, figure.
Perez-Picaso et al., "Linear and cyclic depeptides with antimalarial activity", Bioorganic & Medicinal Chemistry Letters, 22 (2012) 7048-7051.
International Search Report issued on Sep. 29, 2022, from corresponding International Application No. PCT/US21/31246.
Written Opinion of the International Searching Authority issued on Sep. 29, 2022, from corresponding International Application No. PCT/US21/31246.
International Search Report issued on Sep. 2, 2020, from corresponding International Application No. PCT/US20/31998.
Written Opinion of the International Searching Authority issued on Sep. 2, 2020, from corresponding International Application No. PCT/US20/31998.
PubChem CID-136595533 "(2,5-Dioxopyrrol-1-yl) N-(2,5-dihydroxypyrrol-1-yl)-N-(1,3-dioxoisoindol-2-yl)carbamate" Created on Jan. 4, 2019.
PubChem CID-132255576 "(2S)-2-(Imidazole-1-carbonylamino)pentanedioic acid" Created on Jan. 29, 2018.
International Search Report issued on Jul. 31, 2020, from corresponding International Application No. PCT/US20/32025.
Written Opinion of the International Searching Authority issued on Jul. 31, 2020, from corresponding International Application No. PCT/US20/32025.
Yang et al. "MD-2 is required for disulfide HMGB1-dependent TLR4 signaling" The Journal of Experimental Medicine; Published on Jan. 5, 2015; vol. 212; p. 5-14.
Sun et al. "Folic acid derived-P5779 mimetics regulate DAMP-mediated inflammation through disruption of HMGB1:TLR4:MD-2 axes" PLOS One; Published on Feb. 15, 2018; vol. 13; p. 1-14.
International Search Report issued on Sep. 10, 2020, from corresponding International Application No. PCT/US20/31992.
Written Opinion of the International Searching Authority issued on Sep. 10, 2020, from corresponding International Application No. PCT/US20/31992.
PubChem CID-519335 "Methanethioic S-acid" Created on Mar. 27, 2005.
Heffeter et al. "Anticancer Thiosemicarbazones: Chemical Properties, Interaction with Iron Metabolism, and Resistance Development" Antioxidants & Redox Signaling; vol. 30, No. 8, 2019.
International Search Report issued on Sep. 16, 2020, from corresponding International Application No. PCT/US20/31988.
Written Opinion of the International Searching Authority issued on Sep. 16, 2020, from corresponding International Application No. PCT/US20/31988.
PubChem CID-67548889 "Methyl (2S)-1-(imidazole-1-carbonyl)pyrrolidine-2-carboxylate" Created on Nov. 30, 2012.
PubChem CID-1089188 "(2s)-1-(1-Imidazolylcarbonyl)pyrrolidine-2-carboxylic acid benzyl ester" Created on Oct. 26, 2006.
Abo-Dya, N.E., Biswas, S., Basak, A., Avan, I., Alamry, K.A., and Katritzky, A.R., Benzotriazole-Mediated Synthesis of Aza-peptides: En Route to an Aza-Leuenkephalin Analogue. The Journal of Organic Chemistry 78, 3541-3552 (2013).
Avan, I., Hall, C.D., and Katritzky, A.R., Peptidomimetics via modifications of amino acids and peptide bonds. Chemical Society Reviews 43, 3575-3594 (2014).
Andre etal., Tetrahedron Letters, vol. 37, No. 2, pp. 183-186, 1996 (Year: 1996).
The Chemistry of Benzotriazole Derivatives, Monbaliu, Ed., Topic in Heterocyclic Chemistry, Springer, 2016, cover page to p. 2, p. 69 and pp. 95-142 provided (Year: 2016).
Triphosgene Product Data Sheet, Aldrich Chemical Company, 2 pages, 1996 (Year: 1996).
Scientific Update 2014 regarding Deprotection when using Phthalimide, 2 pages, obtained online Aug. 28, 2021 from https://archive.is/20141203032450/http://scientificupdate.co .uk/process-chemistry-information/item/deprotection-removal-of-amine-protecting-groups-phthali mide-and-di methylami nosulphonyl .htm (Year: 2014).
Suppo et al., Org. Synth. 2015, 92, 296-308 (Year: 2015).
Verma et al., Hindawi Publishing Corporation, Journal of Chemistry, vol. 2013, Article ID 329412, 12 pages (Year: 2013).
Boeglin and Lubell, J. Comb. Chem., 7, 864-878 (2005) (Year: 2005).
Che and Marshall, Biopolymers, 2006, 81, 392-406 (Year: 2006).
Mcarthur et al., Syn. Commns., 13:5, 393-401 (1983) (Year: 1983).
Sigma-Aldrich Amino Acids Reference Chart, 2014, downloaded from the internet Aug. 4, 2014 (Year: 2014).
Riemschneider, R. Jacs 1955, 844-8471.
"1824108-09-9", XP093155567, Chemical Abstract Service, Columbus, Ohio, US; Database accession No. 1824108-09-9, Dec. 7, 2015.
L.N. Akimova: "Microstructure of protein X Substituted N-Aminoacyl derivatives of dioxopiperazines". XP093155572, Chemical Abstract Service, Columbus, Ohio, US; Database accession No. 1952:7041, Jan. 1, 1952.
O.L. Salerni et al., "*Synthesis of* [*delta*]*-aminolaevulinic acid analogues as potential antimalarial agents*", Journal of the Chemical Society, Section C: Organic Chemistry. 6015C, vol. 0, No. 0, pp. 1399-1401 (Jan. 1, 1968).
PubChem-SID-13078240, Modify Date: Apr. 27, 2024.

DIMERS FOR USE IN SYNTHESIS OF PEPTIDOMIMETICS

This application claims the benefit of U.S. Provisional Application No. 63/021,803, filed on May 8, 2020, hereby incorporated by reference.

FIELD OF THE INVENTION

The present invention is directed to dimers for use in synthesis of azapeptides and other aza-amino acid conjugates; synthesis of azapeptides and other aza-amino acid conjugates, and uses of azapeptides and other aza-amino acid conjugates in drug discovery, diagnosis, prevention, inhibition, and treatment of diseases.

BACKGROUND OF THE INVENTION

The in vitro and in vivo stability and in vitro and in vivo half-lives of peptides are limited, e.g., by their rate of hydrolysis and enzymatic degradation.

Azapeptides are analogs of peptides. An azapeptide contains a substituted semicarbazide instead of one or more of the amino acid residue(s) of a parent peptide. In other words, one or more of α-carbon atom(s) of the parent peptide are replaced with a nitrogen atom in the azapeptide.

As compared to the parent peptides, azapeptides contain a nitrogen atom instead of one or more of α-carbon atom(s). Due to the reduced reactivity of the carbonyl moiety in the aza-amino acid residue relative to a natural amino acid counterpart, an aza-peptide bond is more stable under the effect of peptidases, and consequently azapeptides are hydrolysed and degraded by peptidases at a slower rate and exhibit, e.g., an improved metabolic stability, than the parent peptides.

However, the rate of formation of the aza-peptide bond is much slower than that of a typical peptide bond. Thus, there is a greater potential of formation of unwanted side products during azapeptide synthesis with aza-amino acids than with conventional amino acids. An additional obstacle in utilizing aza-amino acids in syntheses of azapeptides is the orthogonal functionalization of the two available nitrogen atoms in the hydrazine system.

For these and other reasons, syntheses of azapeptides with aza-amino acids and conventional coupling agents was challenging prior to the present invention.

There is a need for compounds which overcome the limitations of conventional aza-amino acids and/or allow, e.g., for a faster and/or cheaper and/or more efficient syntheses of azapeptides and other aza-amino acid conjugates.

SUMMARY OF THE INVENTION

It is an object of the invention to provide compounds for synthesis of azapeptides and other aza-amino acid conjugates.

It is an object of the invention to provide dimers for synthesis of azapeptides and other aza-amino acid conjugates.

It is a further object of the invention to provide azapeptides and other aza-amino acid conjugates that are more stable and/or more efficacious than their parent peptides.

It is yet an additional object of the invention to provide azapeptide diagnostic and therapeutic agents.

In connection with the above objects and others, the invention provides dimers for use as building blocks or synthons for synthesis of analogues of peptides ("peptidomimetic agents"). The dimers are stable entities and may be stored (e.g., as powder) for extended periods of time without being compromised. In some embodiments, the dimers are stable at 37° C. in an aqueous medium (e.g., an aqueous solution) with a pH of about 7 (e.g., distilled water) for at least 30 minutes, 60 minutes, 90 minutes, 1 hour, 2 hours, 3 hours, 4 hours or 5 hours. As compared to the conventional amino acids and aza-amino acids, the dimers are capable of being activated under milder conditions and at lower temperatures. At the same, peptidomimetic agents assembled from the dimers are more resistant to hydrolysis and enzymatic degradation than the original peptides, and, consequently, may be used in drug discovery, diagnosis, inhibition, prevention and treatment of diseases.

The invention is directed in part to the compounds of Formula (I):

(I)

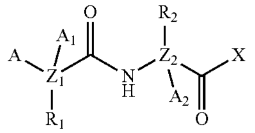

and salts thereof, wherein

- A is N-phthalimidyl (NPhth) or $NR_3R_4$, wherein (i) $R_3$ is H and $R_4$ is tert-butoxycarbonyl (Boc), 9-fluorenylmethoxycarbonyl (Fmoc) or 2-(3,5-dimethoxyphenyl)propan-2-yloxycarbonyl (Ddz) or (ii) $R_3$ and $R_1$ are connected and together form a side chain radical of proline and $R_4$ is tert-butoxycarbonyl, 9-fluorenylmethoxycarbonyl or 2-(3,5-dimethoxyphenyl)propan-2-yloxycarbonyl;
- $A_1$ is H or absent;
- $A_2$ is H or absent;
- X is selected from the group consisting of imidazolyl, benzotriazolyl, S-D, and O-L;
- D is H, Cl, an alkyl, an aryl or a heteroaryl;
- L is an alkyl, imidazolyl or benzotriazolyl;
- $R_1$ and $R_2$ is each independently selected from the group consisting of side chain radicals of amino acids;
- $Z_1$ and $Z_2$ is each independently C or N. In these compounds, $A_1$ is absent when $Z_1$ is N; and $A_2$ is absent when $Z_2$ is N.

The invention is also directed in part to the compounds of Formula (I):

(I)

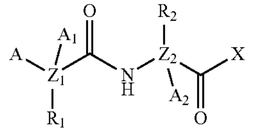

and salts thereof, wherein

- A is N-phthalimidyl or $NR_3R_4$, wherein (i) $R_3$ is H and $R_4$ is tert-butoxycarbonyl, 9-fluorenylmethoxycarbonyl or 2-(3,5-dimethoxyphenyl)propan-2-yloxycarbonyl or (ii) $R_3$ and $R_1$ are connected and together form a side chain radical of proline and $R_4$ is tert-butoxycarbonyl, 9-fluorenylmethoxycarbonyl or 2-(3,5-dimethoxyphenyl)propan-2-yloxycarbonyl;
- $A_1$ is H or absent;
- $A_2$ is H or absent;

X is selected from the group consisting of imidazolyl, benzotriazolyl, S-D, and O-L;

D is H, Cl, an alkyl, an aryl or a heteroaryl;

L is an alkyl, imidazolyl or benzotriazolyl;

$R_1$ and $R_2$ is each independently selected from the group consisting of side chain radicals of amino acids;

$Z_1$ and $Z_2$ is each independently C or N, and at least one of $Z_1$ and $Z_2$ is N. In these compounds, when $Z_1$ is N, $A_1$ is absent; and when $Z_2$ is N, $A_2$ is absent.

The invention is also directed in part to the compounds of Formula (I):

(I)

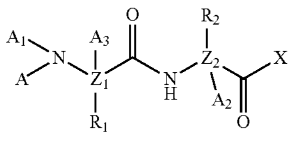

and salts thereof, wherein

A is tert-butoxycarbonyl, 9-fluorenylmethoxycarbonyl, or 2-(3,5-dimethoxyphenyl)propan-2-yloxycarbonyl;

$A_1$ is H;

$A_2$ is H or absent;

$A_3$ is H or absent;

X is selected from the group consisting of imidazolyl, benzotriazolyl, S-D, and O-L;

D is H, Cl, an alkyl, an aryl or a heteroaryl;

L is an alkyl, imidazolyl or benzotriazolyl;

$R_1$ and $R_2$ is each independently selected from the group consisting of side chain radicals of amino acids;

$Z_1$ and $Z_2$ is each independently C or N. In these compounds, when $Z_1$ is N, $A_3$ is absent; and when $Z_2$ is N, $A_2$ is absent.

The invention is also directed in part to the compounds of Formula (I):

(I)

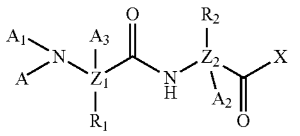

and salts thereof, wherein

A is tert-butoxycarbonyl, 9-fluorenylmethoxycarbonyl, or 2-(3,5-dimethoxyphenyl)propan-2-yloxycarbonyl;

$A_1$ is H;

$A_2$ is H or absent;

$A_3$ is H or absent;

X is selected from the group consisting of imidazolyl, benzotriazolyl, S-D, and O-L;

D is H, Cl, an alkyl, an aryl or a heteroaryl;

L is an alkyl, imidazolyl or benzotriazolyl;

$R_1$ and $R_2$ is each independently selected from the group consisting of side chain radicals of amino acids;

$Z_1$ and $Z_2$ is each independently C or N, and at least one of $Z_1$ and $Z_2$ is N. In these compounds, when $Z_1$ is N, $A_3$ is absent; and when $Z_2$ is N, $A_2$ is absent.

The invention is further directed in part to the compounds of Formula (I):

(I)

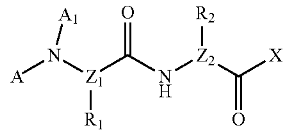

and salts thereof, wherein

A is tert-butoxycarbonyl, 9-fluorenylmethoxycarbonyl, or 2-(3,5-dimethoxyphenyl)propan-2-yloxycarbonyl;

$A_1$ is H;

X is selected from the group consisting of imidazolyl, benzotriazolyl, S-D, and O-L;

D is H, Cl, an alkyl, an aryl or a heteroaryl;

L is an alkyl, imidazolyl or benzotriazolyl;

$R_1$ and $R_2$ is each independently selected from the group consisting of side chain radicals of amino acids;

$Z_1$ and $Z_2$ are both N.

The invention is also directed in part to the compounds of Formula (I):

(I)

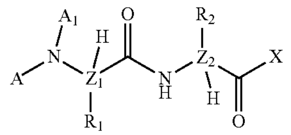

and salts thereof, wherein

A is tert-butoxycarbonyl (Boc), 9-fluorenylmethoxycarbonyl (Fmoc), or 2-(3,5-dimethoxyphenyl)propan-2-yloxycarbonyl (Ddz);

$A_1$ is H;

X is selected from the group consisting of imidazolyl, benzotriazolyl, S-D, and O-L;

D is H, Cl, an alkyl, an aryl or a heteroaryl;

L is an alkyl, imidazolyl, benzotriazolyl;

$R_1$ and $R_2$ is each independently selected from the group consisting of side chain radicals of amino acids;

$Z_1$ and $Z_2$ are both C.

The invention is further directed in part to compounds of Formula (I), wherein $A_1$ is H; A is tert-butoxycarbonyl or 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is tert-butoxycarbonyl or 9-fluorenylmethoxycarbonyl; X is selected from the group consisting of imidazolyl and benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is tert-butoxycarbonyl or 9-fluorenylmethoxycarbonyl; X is S-D; D is H, Cl, an alkyl, an aryl or a heteroaryl; $R_1$ and $R_2$ is each independently selected from the group consisting of side chain radicals of amino acids; $Z_1$ and $Z_2$ is each independently C or N; and at least one of $Z_1$ and $Z_2$ is N. The invention specifically encompasses, e.g., compounds of Formula (I), wherein $A_1$ is H; A is tert-butoxycarbonyl or 9-fluorenylmethoxycarbonyl; X is S-D; D an alkyl (e.g., ethyl); $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is tert-butoxycarbonyl or 9-fluorenylmethoxycarbonyl; X is O-L; L is an alkyl, imidazolyl, or benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N. The invention specifically encompasses, e.g., compounds of Formula (I), wherein $A_1$ is H; A is tert-butoxycarbonyl or 9-fluorenylmethoxycarbonyl; X is O-L; L is imidazolyl or benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N The invention is also directed in part to compounds of Formula (I), wherein $A_1$ is H; A is tert-butoxycarbonyl; X is selected from the group consisting of imidazolyl, benzotriazolyl, S-D and O-L; D is H, Cl, an alkyl, an aryl or a heteroaryl; L is an alkyl, imidazolyl, benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is tert-butoxycarbonyl; X is selected from the group consisting of imidazolyl and benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is tert-butoxycarbonyl; X is S-D; D is H, Cl, an alkyl, an aryl or a heteroaryl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is tert-butoxycarbonyl; X is O-L; L is an alkyl, imidazolyl, or benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl, benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is 9-fluorenylmethoxycarbonyl; X is selected from the group consisting of imidazolyl and benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A is 9-fluorenylmethoxycarbonyl; X is S-D; D is H, Cl, an alkyl, an aryl or a heteroaryl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is also directed in part to compounds of Formula (I), wherein $A_1$ is H; A 9-fluorenylmethoxycarbonyl; X is O-L; L is an alkyl, imidazolyl, or benzotriazolyl; $R_1$ and $R_2$ is each independently selected from the group consisting of side chain radicals of amino acids; $Z_1$ and $Z_2$ is each independently C or N; and at least one of $Z_1$ and $Z_2$ is N.

The invention is further directed in part to the compounds of Formula (I):

(I)

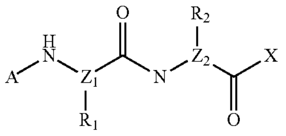

and salts thereof, wherein A is tert-butoxycarbonyl, 9-fluorenylmethoxycarbonyl, or 2-(3,5-dimethoxyphenyl)propan-2-yloxycarbonyl;

X is selected from the group consisting of imidazolyl, benzotriazolyl, S-D, and O-L;

D is H, Cl, an alkyl, an aryl or a heteroaryl;

L is an alkyl, imidazolyl or benzotriazolyl;

$R_1$ and $R_2$ is each independently selected from the group consisting of side chain radicals of amino acids;

$Z_1$ and $Z_2$ is each independently C or N, and at least one of $Z_1$ and $Z_2$ is N.

The invention is also directed in part to compounds of Formula (IA):

(IA)

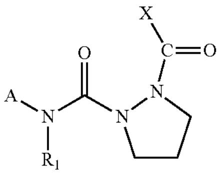

and salts thereof, wherein

A is N-phthalimidyl or $NR_3R_4$, wherein (i) $R_3$ is H and $R_4$ is tert-butoxycarbonyl, 9-fluorenylmethoxycarbonyl or 2-(3,5-dimethoxyphenyl)propan-2-yloxycarbonyl or (ii) $R_3$ and $R_1$ are connected and together form a side chain radical of proline and $R_4$ is tert-butoxycarbonyl, 9-fluorenylmethoxycarbonyl or 2-(3,5-dimethoxyphenyl)propan-2-yloxycarbonyl;

X is selected from the group consisting of imidazolyl, benzotriazolyl, S-D and O-L;

D is H, Cl, an alkyl, an aryl or a heteroaryl;

L is an alkyl, imidazolyl or benzotriazolyl;

$R_1$ is selected from the group consisting of side chain radicals of amino acids.

The invention is further directed in part to compounds of Formula (IA):

(IA)

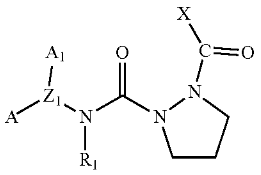

and salts thereof, wherein

A is tert-butoxycarbonyl, 9-fluorenylmethoxycarbonyl, or 2-(3,5-dimethoxyphenyl)propan-2-yloxycarbonyl;

$A_1$ is H;

X is selected from the group consisting of imidazolyl, benzotriazolyl, S-D and O-L;

D is H, Cl, an alkyl, an aryl or a heteroaryl;

L is an alkyl, imidazolyl, benzotriazolyl;

$R_1$ is selected from the group consisting of side chain radicals of amino acids; $Z_1$ is C or N.

The invention is also directed in part to compounds of Formula (IA), wherein $A_1$ is H; A is tert-butoxycarbonyl or 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl, benzotriazolyl; $R_1$ is selected from the group consisting of side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is tert-butoxycarbonyl or 9-fluorenylmethoxycarbonyl; X is selected from the group consisting of imidazolyl or benzotriazolyl; $R_1$ is selected from the group consisting side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is tert-butoxycarbonyl or 9-fluorenylmethoxycarbonyl; X is S-D; D is H, Cl, an alkyl, an aryl or a heteroaryl; $R_1$ is selected from the group consisting of side chain radicals of amino acids; $Z_1$ and $Z_2$ is each independently C or N; and at least one of $Z_1$ and $Z_2$ is N. The invention specifically encompasses, e.g., compounds of Formula (IA), wherein $A_1$ is H; A is tert-butoxycarbonyl or 9-fluorenylmethoxycarbonyl; X is S-D; D is an alkyl (e.g., ethyl); $R_1$ is selected from the group consisting of side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is tert-butoxycarbonyl; X is O-L; L is an alkyl, imidazolyl, benzotriazolyl; $R_1$ and $R_2$ is each independently selected from the group consisting of side chain radicals of amino acids; $Z_1$ and $Z_2$ is each independently C or N, at least one of $Z_1$ and $Z_2$ is N. The invention specifically encompasses of Formula (IA), wherein $A_1$ is H; A is tert-butoxycarbonyl; X is O-L; L is imidazolyl or benzotriazolyl; $R_1$ and $R_2$ is each independently selected from the group consisting of side chain radicals of amino acids; $Z_1$ and $Z_2$ is each independently C or N, at least one of $Z_1$ and $Z_2$ is N The invention is also directed in part to compounds of Formula (IA), wherein $A_1$ is H; A is tert-butoxycarbonyl; X is selected from the group consisting of imidazolyl, benzotriazolyl, S-D and O-L; D is H, Cl, an alkyl, an aryl or a heteroaryl; L is an alkyl, imidazolyl, benzotriazolyl; $R_1$ is selected from the group consisting of side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is tert-butoxycarbonyl; X is selected from the group consisting of imidazolyl or benzotriazolyl; $R_1$ is selected from the group consisting side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is tert-butoxycarbonyl; X is S-D; D is H, Cl, an alkyl, an aryl or a heteroaryl; $R_1$ is selected from the group consisting of side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is tert-butoxycarbonyl; X is O-L; L is an alkyl, imidazolyl, benzotriazolyl; $R_1$ and $R_2$ is each independently selected from the group consisting of side chain radicals of amino acids; $Z_1$ and $Z_2$ is each independently C or N, at least one of $Z_1$ and $Z_2$ is N.

The invention is also directed in part to compounds of Formula (IA), wherein $A_1$ is H; A is 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl, benzotriazolyl; $R_1$ is selected from the group consisting of side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is 9-fluorenylmethoxycarbonyl; X is selected from the group consisting of imidazolyl or benzotriazolyl; $R_1$ is selected from the group consisting side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is 9-fluorenylmethoxycarbonyl; X is S-D; D is H, Cl, an alkyl, an aryl or a heteroaryl; $R_1$ is selected from the group consisting of side chain radicals of amino acids; $Z_1$ and $Z_2$ is each independently C or N; and at least one of $Z_1$ and $Z_2$ is N.

The invention is also directed in part to compounds of Formula (IA), wherein $A_1$ is H; A is 9-fluorenylmethoxycarbonyl; X is O-L; L is an alkyl, imidazolyl, benzotriazolyl; $R_1$ and $R_2$ is each independently selected from the group consisting of side chain radicals of amino acids; $Z_1$ and $Z_2$ is each independently C or N, at least one of $Z_1$ and $Z_2$ is N.

The invention is also directed in part to compounds of Formula (IA):

(IA)

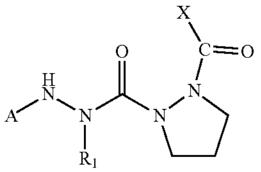

and salts thereof, wherein A is tert-butoxycarbonyl, 9-fluorenylmethoxycarbonyl, 2-(3,5-dimethoxyphenyl)propan-2-yloxycarbonyl;

X is selected from the group consisting of imidazolyl, benzotriazolyl, S-D and O-L;

D is H, Cl, an alkyl, an aryl or a heteroaryl;

L is an alkyl, imidazolyl or benzotriazolyl;

$R_1$ is selected from the group consisting of side chain radicals of amino acids.

The invention is also directed in part to compounds of Formula (II):

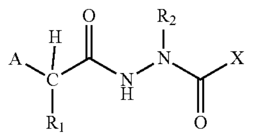

(II)

and salts thereof, wherein

A is N-phthalimidyl or $NR_3R_4$, wherein (i) $R_3$ is H and $R_4$ is tert-butoxycarbonyl, 9-fluorenylmethoxycarbonyl or 2-(3,5-dimethoxyphenyl)propan-2-yloxycarbonyl or (ii) $R_3$ and $R_1$ are connected and together form a side chain radical of proline and $R_4$ is tert-butoxycarbonyl, 9-fluorenylmethoxycarbonyl or 2-(3,5-dimethoxyphenyl)propan-2-yloxycarbonyl;

X is selected from the group consisting of imidazolyl, benzotriazolyl, S-D and O-L;

D is H, Cl, an alkyl, an aryl or a heteroaryl;

L is an alkyl, imidazolyl or benzotriazolyl; and $R_1$ and $R_2$ is each independently selected from the group consisting of side chain radicals of amino acids.

The invention is also directed in part to compounds of Formula (II):

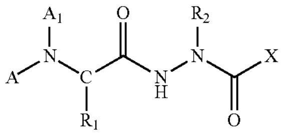

(II)

and salts thereof, wherein

A is tert-butoxycarbonyl, 9-fluorenylmethoxycarbonyl, or 2-(3,5-dimethoxyphenyl)propan-2-yloxycarbonyl;

$A_1$ is H;

X is selected from the group consisting of imidazolyl, benzotriazolyl, S-D and O-L;

D is H, Cl, an alkyl, an aryl or a heteroaryl;

L is an alkyl, imidazolyl or benzotriazolyl; and $R_1$ and $R_2$ is each independently selected from the group consisting of side chain radicals of amino acids.

The invention is also directed in part to compounds of Formula (II), wherein $A_1$ is H; A is tert-butoxycarbonyl or 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (II), wherein $A_1$ is H; A is tert-butoxycarbonyl or 9-fluorenylmethoxycarbonyl; X is selected from the group consisting of imidazolyl and benzotriazolyl; and $R_1$ and $R_2$ is each independently selected from the group consisting of side chain radicals of amino acids.

The invention is also directed in part to compounds of Formula (II), wherein $A_1$ is H; A is tert-butoxycarbonyl or 9-fluorenylmethoxycarbonyl; X is S-D; D is H, Cl, an alkyl, an aryl or a heteroaryl; and $R_1$ and $R_2$ is each independently selected from the group consisting of side chain radicals of amino acids. The invention specifically encompasses compounds of Formula (II), wherein $A_1$ is H; A is tert-butoxycarbonyl or 9-fluorenylmethoxycarbonyl; X is S-D; D is an alkyl (e.g., ethyl); and $R_1$ and $R_2$ is each independently selected from the group consisting of side chain radicals of amino acids.

The invention is also directed in part to compounds of Formula (II), wherein $A_1$ is H; A is tert-butoxycarbonyl or 9-fluorenylmethoxycarbonyl; X is O-L; L is an alkyl, imidazolyl or benzotriazolyl; $R_1$ and $R_2$ is each independently selected from the group consisting of side chain radicals of amino acids. The invention specifically encompasses compounds of Formula (II), wherein $A_1$ is H; A is tert-butoxycarbonyl or 9-fluorenylmethoxycarbonyl; X is O-L; L is imidazolyl or benzotriazolyl; $R_1$ and $R_2$ is each independently selected from the group consisting of side chain radicals of amino acids.

The invention is also directed in part to compounds of Formula (II), wherein $A_1$ is H; A is tert-butoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (II), wherein $A_1$ is H; A is tert-butoxycarbonyl; X is selected from the group consisting of imidazolyl and benzotriazolyl; and $R_1$ and $R_2$ is each independently selected from the group consisting of side chain radicals of amino acids.

The invention is also directed in part to compounds of Formula (II), wherein $A_1$ is H; A is tert-butoxycarbonyl; X is S-D; D is H, Cl, an alkyl, an aryl or a heteroaryl; and $R_1$ and $R_2$ is each independently selected from the group consisting of side chain radicals of amino acids.

The invention is also directed in part to compounds of Formula (II), wherein $A_1$ is H; A is tert-butoxycarbonyl; X is O-L; L is an alkyl, imidazolyl or benzotriazolyl; $R_1$ and $R_2$ is each independently selected from the group consisting of side chain radicals of amino acids.

The invention is also directed in part to compounds of Formula (II), wherein $A_1$ is H; A is 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (II), wherein $A_1$ is H; A is 9-fluorenylmethoxycarbonyl; X is selected from the group consisting of imidazolyl and benzotriazolyl; and $R_1$ and $R_2$ is each independently selected from the group consisting of side chain radicals of amino acids.

The invention is also directed in part to compounds of Formula (II), wherein $A_1$ is H; A is 9-fluorenylmethoxycarbonyl; X is S-D; D is H, Cl, an alkyl, an aryl or a heteroaryl; and $R_1$ and $R_2$ is each independently selected from the group consisting of side chain radicals of amino acids.

The invention is also directed in part to compounds of Formula (II), wherein $A_1$ is H; A is 9-fluorenylmethoxycarbonyl; X is O-L; L is an alkyl, imidazolyl or benzotriazolyl; $R_1$ and $R_2$ is each independently selected from the group consisting of side chain radicals of amino acids.

The invention is further directed in part to the compounds of Formula (IB):

(IB)

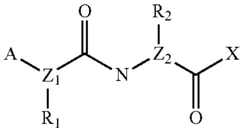

and salts thereof, wherein A is N-phthalimidyl;

X is selected from the group consisting of imidazolyl, benzotriazolyl, S-D, and O-L;

D is H, Cl, an alkyl, an aryl or a heteroaryl;

L is an alkyl, imidazolyl or benzotriazolyl;

$R_1$ and $R_2$ is each independently selected from the group consisting of side chain radicals of amino acids;

$Z_1$ is N; and $Z_2$ is CH or N.

The invention is also directed in part to the compounds of Formula (IB):

(IB)

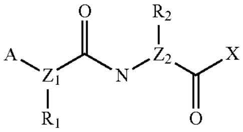

and salts thereof, wherein A is N-phthalimidyl;

X is selected from the group consisting of imidazolyl, benzotriazolyl, S-D, and O-L;

D is H, Cl, an alkyl, an aryl or a heteroaryl;

L is an alkyl, imidazolyl or benzotriazolyl;

$R_1$ and $R_2$ is each independently selected from the group consisting of side chain radicals of amino acids;

$Z_1$ is CH or N, and $Z_2$ is N.

The invention is also directed in part to compounds of Formula (IC):

(IC)

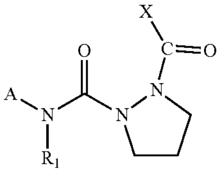

and salts thereof, wherein A is N-phthalimidyl;

X is selected from the group consisting of imidazolyl, benzotriazolyl, S-D and O-L;

D is H, Cl, an alkyl, an aryl or a heteroaryl;

L is an alkyl, imidazolyl or benzotriazolyl;

$R_1$ is selected from the group consisting of side chain radicals of amino acids.

The invention is also directed in part to compounds of Formula (III):

(III)

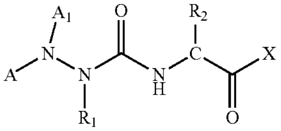

and salts thereof, wherein

A is N-phthalimidyl, tert-butoxycarbonyl, 9-fluorenylmethoxycarbonyl, or 2-(3,5-dimethoxyphenyl)propan-2-yloxycarbonyl;

$A_1$ is H;

X is selected from the group consisting of imidazolyl, benzotriazolyl, S-D and O-L;

D is H, Cl, an alkyl, an aryl or a heteroaryl;

L is an alkyl, imidazolyl or benzotriazolyl; and $R_1$ and $R_2$ is each independently selected from the group consisting of side chain radicals of amino acids.

The invention is also directed in part to compounds of Formula (III), wherein $A_1$ is H; A is tert-butoxycarbonyl or 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (III), wherein $A_1$ is H; A is tert-butoxycarbonyl or 9-fluorenylmethoxycarbonyl; X is selected from the group consisting of imidazolyl and benzotriazolyl; and $R_1$ and $R_2$ is each independently selected from the group consisting of H and side chain radicals of amino acids.

The invention is also directed in part to compounds of Formula (III), wherein $A_1$ is H; A is tert-butoxycarbonyl or 9-fluorenylmethoxycarbonyl; X is S-D; D is H, Cl, an alkyl, an aryl or a heteroaryl; and $R_1$ and $R_2$ is each independently selected from the group consisting of side chain radicals of amino acids. The invention specifically encompasses compounds of Formula (III), wherein $A_1$ is H; A is tert-butoxycarbonyl or 9-fluorenylmethoxycarbonyl; X is S-D; D is an alkyl (e.g., ethyl); and $R_1$ and $R_2$ is each independently selected from the group consisting of side chain radicals of amino acids.

The invention is also directed in part to compounds of Formula (III), wherein $A_1$ is H; A is tert-butoxycarbonyl or 9-fluorenylmethoxycarbonyl; X is O-L; L is an alkyl, imidazolyl or benzotriazolyl; $R_1$ and $R_2$ is each independently selected from the group consisting of side chain radicals of amino acids. The invention specifically encompasses compounds of Formula (III), wherein $A_1$ is H; A is tert-butoxycarbonyl or 9-fluorenylmethoxycarbonyl; X is O-L; L is imidazolyl or benzotriazolyl; $R_1$ and $R_2$ is each independently selected from the group consisting of side chain radicals of amino acids.

The invention is also directed in part to compounds of Formula (III), wherein $A_1$ is H; A is tert-butoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (III), wherein $A_1$ is H; A is tert-butoxycarbonyl; X is selected from the group consisting of imidazolyl and benzotriazolyl; and $R_1$ and $R_2$ is each independently selected from the group consisting of H and side chain radicals of amino acids.

The invention is also directed in part to compounds of Formula (III), wherein $A_1$ is H; A is tert-butoxycarbonyl; X is S-D; D is H, Cl, an alkyl, an aryl or a heteroaryl; and $R_1$ and $R_2$ is each independently selected from the group consisting of side chain radicals of amino acids.

The invention is also directed in part to compounds of Formula (III), wherein $A_1$ is H; A is tert-butoxycarbonyl; X is O-L; L is an alkyl, imidazolyl or benzotriazolyl; $R_1$ and $R_2$ is each independently selected from the group consisting of side chain radicals of amino acids.

The invention is also directed in part to compounds of Formula (III), wherein $A_1$ is H; A is 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (III), wherein $A_1$ is H; A is 9-fluorenylmethoxycarbonyl; X is selected from the group consisting of imidazolyl and benzotriazolyl; and $R_1$ and $R_2$ is each independently selected from the group consisting of H and side chain radicals of amino acids.

The invention is also directed in part to compounds of Formula (III), wherein $A_1$ is H; A is 9-fluorenylmethoxycarbonyl; X is S-D; D is H, Cl, an alkyl, an aryl or a heteroaryl; and $R_1$ and $R_2$ is each independently selected from the group consisting of side chain radicals of amino acids.

The invention is also directed in part to compounds of Formula (III), wherein $A_1$ is H; A is 9-fluorenylmethoxycarbonyl; X is O-L; L is an alkyl, imidazolyl or benzotriazolyl; $R_1$ and $R_2$ is each independently selected from the group consisting of side chain radicals of amino acids.

The invention is also directed in part to compounds of Formula (III):

(III)

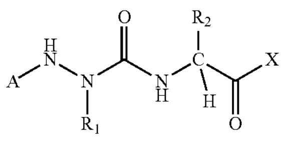

and salts thereof, wherein A is tert-butoxycarbonyl, 9-fluorenylmethoxycarbonyl, or 2-(3,5-dimethoxyphenyl)propan-2-yloxycarbonyl;

X is selected from the group consisting of imidazolyl, benzotriazolyl, S-D and O-L;

D is H, Cl, an alkyl, an aryl or a heteroaryl;

L is an alkyl, imidazolyl or benzotriazolyl; and $R_1$ and $R_2$ is each independently selected from the group consisting of side chain radicals of amino acids.

The invention is also directed in part to compounds of Formula (IIIA):

(IIIA)

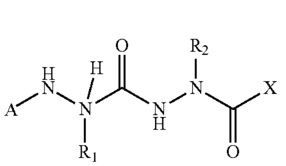

and salts thereof, wherein A is tert-butoxycarbonyl, 9-fluorenylmethoxycarbonyl, or 2-(3,5-dimethoxyphenyl)propan-2-yloxycarbonyl;

X is selected from the group consisting of imidazolyl, benzotriazolyl, S-D and O-L;

D is H, Cl, an alkyl, an aryl or a heteroaryl;

L is an alkyl, imidazolyl or benzotriazolyl; and $R_1$ and $R_2$ is each independently selected from the group consisting of side chain radicals of amino acids.

The invention is also directed in part to compounds of Formula (IV):

(IV)

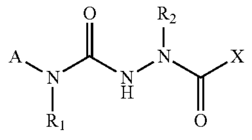

and salts thereof, wherein

A is N-phthalimidyl or $NR_3R_4$, wherein (i) $R_3$ is H and $R_4$ is tert-butoxycarbonyl, 9-fluorenylmethoxycarbonyl or 2-(3,5-dimethoxyphenyl)propan-2-yloxycarbonyl or (ii) $R_3$ and $R_1$ are connected and together form a side chain radical of proline and $R_4$ is tert-butoxycarbonyl, 9-fluorenylmethoxycarbonyl or 2-(3,5-dimethoxyphenyl)propan-2-yloxycarbonyl; X is selected from the group consisting of imidazolyl, benzotriazolyl, S-D or O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (IV):

(IV)

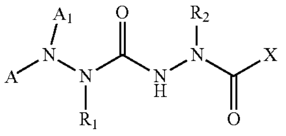

and salts thereof, wherein

A is tert-butoxycarbonyl, 9-fluorenylmethoxycarbonyl, 2-(3,5-dimethoxyphenyl)propan-2-yloxycarbonyl; $A_1$ is H, X is selected from the group consisting of imidazolyl, benzotriazolyl, S-D or O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (IV), wherein $A_1$ is H; A is tert-butoxycarbonyl or 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (IV), wherein $A_1$ is H; A is tert-butoxycarbonyl or 9-fluorenylmethoxycarbonyl; X is selected from the group consisting of imidazolyl and benzotriazolyl; and $R_1$ and $R_2$ is each independently selected from the group consisting of side chain radicals of amino acids.

The invention is also directed in part to compounds of Formula (IV), wherein $A_1$ is H; A is tert-butoxycarbonyl or 9-fluorenylmethoxycarbonyl; X is S-D; D is H, Cl, an alkyl, an aryl or a heteroaryl; and $R_1$ and $R_2$ is each independently selected from the group consisting of side chain radicals of amino acids. The invention specifically encompasses compounds of Formula (IV), wherein $A_1$ is H; A is tert-butoxycarbonyl or 9-fluorenylmethoxycarbonyl; X is S-D; D is an alkyl (e.g., ethyl); and $R_1$ and $R_2$ is each independently selected from the group consisting of side chain radicals of amino acids.

The invention is also directed in part to compounds of Formula (IV), wherein $A_1$ is H; A is tert-butoxycarbonyl or 9-fluorenylmethoxycarbonyl; X is O-L; L is an alkyl, imidazolyl, or benzotriazolyl; $R_1$ and $R_2$ is each independently selected from the group consisting of side chain radicals of amino acids. The invention is specifically directed to compounds of Formula (IV), wherein $A_1$ is H; A is tert-butoxycarbonyl or 9-fluorenylmethoxycarbonyl; X is O-L; L is imidazolyl or benzotriazolyl; $R_1$ and $R_2$ is each independently selected from the group consisting of side chain radicals of amino acids.

The invention is also directed in part to compounds of Formula (IV), wherein $A_1$ is H; A is tert-butoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (IV), wherein $A_1$ is H; A is tert-butoxycarbonyl; X is selected from the group consisting of imidazolyl and benzotriazolyl; and $R_1$ and $R_2$ is each independently selected from the group consisting of side chain radicals of amino acids.

The invention is also directed in part to compounds of Formula (IV), wherein $A_1$ is H; A is tert-butoxycarbonyl; X is S-D; D is H, Cl, an alkyl, an aryl or a heteroaryl; and $R_1$ and $R_2$ is each independently selected from the group consisting of side chain radicals of amino acids.

The invention is also directed in part to compounds of Formula (IV), wherein $A_1$ is H; A is tert-butoxycarbonyl; X is O-L; L is an alkyl, imidazolyl, or benzotriazolyl; $R_1$ and $R_2$ is each independently selected from the group consisting of side chain radicals of amino acids.

The invention is also directed in part to compounds of Formula (IV), wherein $A_1$ is H; A is 9-fluorenylmethoxycarbonyl; X is selected from the group consisting of imidazolyl, benzotriazolyl, S-D and O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (IV), wherein $A_1$ is H; A is 9-fluorenylmethoxycarbonyl; X is selected from the group consisting of imidazolyl and benzotriazolyl; and $R_1$ and $R_2$ is each independently selected from the group consisting of side chain radicals of amino acids.

The invention is also directed in part to compounds of Formula (IV), wherein $A_1$ is H; A is 9-fluorenylmethoxycarbonyl; X is S-D; D is H, Cl, an alkyl, an aryl or a heteroaryl; and $R_1$ and $R_2$ is each independently selected from the group consisting of side chain radicals of amino acids.

The invention is also directed in part to compounds of Formula (IV), wherein $A_1$ is H; A is 9-fluorenylmethoxycarbonyl; X is O-L; L is an alkyl, imidazolyl, or benzotriazolyl; $R_1$ and $R_2$ is each independently selected from the group consisting of side chain radicals of amino acids.

The invention is also directed in part to compounds of Formula (IV):

(IV)

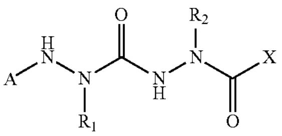

and salts thereof, wherein A is tert-butoxycarbonyl, 9-fluorenylmethoxycarbonyl, 2-(3,5-dimethoxyphenyl)propan-2-yloxycarbonyl; X is selected from the group consisting of imidazolyl, benzotriazolyl, S-D or O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

The invention is also directed in part to compounds of Formula (IV):

(IV)

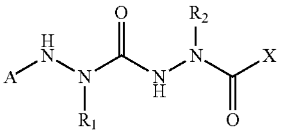

and salts thereof, wherein A is N-phthalimidyl; X is selected from the group consisting of imidazolyl, benzotriazolyl, S-D or O-L; D is H, Cl, an alkyl, an aryl or a heteroaryl; L is an alkyl, imidazolyl or benzotriazolyl; and $R_1$ and $R_2$ is each independently selected from the group consisting of side chain radicals of amino acids.

In the compounds of the invention, $R_1$ and $R_2$ could each independently be, e.g., a side chain radical of a natural amino acid or a side chain radical of an unnatural amino acid.

The side chain radical of the natural amino acid could be selected, e.g., from the group consisting of side chain radicals of aspartic acid, phenylalanine, alanine, histidine, glutamic acid, tryptophan, valine, leucine, lysine, methionine, threonine, tyrosine, isoleucine (including, R-isoleucine, S-isoleucine and RS-isoleucine), arginine, glycine, asparagine, serine, proline and glutamine. In some of the compounds of the invention, $R_1$ and $R_2$ could each independently be selected from the group consisting of side chain radicals of glycine, alanine, valisone, serine, threonine, asparagine, glutamine, cysteine, $CH_2$—SeH (SeH), isoleucine, leucine, methionine, lysine, aspartic acid, glutamic acid, arginine, phenylalanine, tyrosine, tryptophan, histidine, and proline.

The side chain of the unnatural amino acid could be selected, e.g., from the group consisting of side chain radicals of β-amino acids (e.g., L-β-homotyrosine, β-alanine, L-β-homoasparagine, L-β-homoalanine, L-β-homophenylalanine, L-β-homoproline, L-β-holysine, L-β-homorarginine, L-β-proline, etc.), aliphatic amino acids (e.g., 6-aminohexanoic acid, 2-amino-3-methoxybutanoic acid, 1-aminocyclopentane-1-carboxylic acid, 2-(aminooxy)acetic acid, 6-aminohexanoic acid, 2-[2-(amino)-ethoxy]-ethoxy}acetic acid), β-cyclohexyl-L-alanine, 6-aminohexanoic acid, L-α,β-diaminopropionic acid, L-propargylglycine, L-α,β-diaminopropionic acid, α-aminoisobutyric acid, β-(2-pyridyl)-L-alanine, β-(3-pyridyl)-L-alanine, β-cyclopropyl-L-alanine, β-t-butyl-L-alanine, (2,4-dinitrophenyl))-L-α,β-diaminopropionic acid, (allyloxycarbonyl)-L-α,β-diaminopropionic acid, D-α,β-diaminopropionic acid, L-α,β-diaminopropionic acid, (N-T-1-(4,4-dimethyl-2,6-dioxocyclohex-1-ylidene)ethyl)-L-α,γ-diaminobutyric acid, (N-γ-4-methyltrityl)-L-α,γ-diaminobutyric acid, L-α,γ-diaminobutyric acid, 4-fluoro-L-phenylglycine, 5,5,5-trifluoro-DL-leucine, epsilon-aminohexanoic-OH, L-α-t-butylglycine, L-2-amino-3-(dimethylamino)propionic acid, L-2-aminocaproic acid, L-allylglycine, lysine azide, (Nδ-4-methyltrityl)-L-ornithine, Arg(Me)(Pbf)-OH, dimethyl-L-arginine (symmetrical and unsymmetrical), L-2-amino-3-guanidinopropionic acid, L-citrulline, F-acetyl-L-lysine, Lys(ivDde)-OH, Lys(Me)2-OH·HCl, Lys(Me3)-OHchloride, α-methyl-DL-glutamic acid, γ-carboxy-L-glutamic acid γ,γ-di-t-butyl ester, (N-γ-ethyl)-L-glutamine, 2,6-diaminopimelic acid, Glu(OAll)-OH, L-cysteic acid, α-methyl-DL-methionine, DL-buthionine, L-cysteic acid, L-selenomethionine, S-[2-(4-pyridyl)ethyl]-L-cysteine, S-[2-(4-pyridyl)ethyl]-L-cysteine, S-diphenylmethyl-L-cysteine, S-trityl-L-homocysteine, S-trityl-L-penicillamine, (Se-p-methoxybenzyl)-L-selenocysteine, R-hydroxyphenylalanine, 2-cyano-L-phenylalanine, L-thyroxine, O-methyl-L-tyrosine, R-methyl-DL-phenylalanine, 2-cyano-L-phenylalanine, L-thyroxine, O-methyl-L-tyrosine, R-methyl-DL-phenylalanine, 2-cyano-L-phenylalanine, 3,4-dichloro-L-phenylalanine, 3,4-difluoro-L-phenylalanine, 3,4-dihydroxy-L-phenylalanine, 3,4-dihydroxy-phenylalanine, 3-amino-L-tyrosine, 3-chloro-L-tyrosine, 3-fluoro-DL-tyrosine, 3-nitro-L-tyrosine, 4-amino-L-phenylalanine, 4-aminomethyl-L-phenylalanine, 4-(phosphonomethyl)-phenylalanine, 4-benzoyl-D-phenylalanine, 4-bis(2-chloroethyl)amino-L-phenylalanine, 4-cyano-L-phenylalanine, 4-fluoro-L-phenylalanine, 4-iodo-L-phenylalanine, DL-m-tyrosine, 2,6-dimethyl-tyrosine, L-homophenylalanine, O-methyl-L-tyrosine, Phe(4-guanidino)-OH, O-benzyl-L-phosphotyrosine, (2S,3R)-3-phenylpyrrolidine-2-carboxylic acid, (2S,4S)-4-phenyl-pyrrolidine-2-carboxylic acid, (2S,3aS,7aS)-Octahydro-1H-indole-2-carboxylic acid, (2S,3R)-3-phenylpyrrolidine-2-carboxylic acid, (2S,4R)-(−)-4-t-butoxypyrrolidine-2-carboxylic acid, trans-4-Fluoro-L-proline, (3S,4S)-4-amino-3-hydroxy-6-methylheptanoic acid, 4-amino-3-hydroxybutanoic acid, L-α-methylserine, (2S,3S)-2-amino-3-methoxybutanoic acid, Thr(β-D-GlcNAc(Ac)3)—OH, O-benzyl-L-phosphoserine, O-benzyl-D-phosphothreonine, O-benzyl-L-phosphothreonine, 4-methyl-DL-tryptophan, 6-fluoro-DL-tryptophan, 6-methyl-DL-tryptophan, DL-7-azatryptophan, (R)-7-Azatryptophan, 5-benzyloxy-DL-tryptophan, 5-bromo-DL-tryptophan, 5-chloro-DL-tryptophan, 5-fluoro-DL-tryptophan, 5-hydroxy-L-tryptophan, 5-methoxy-L-tryptophan, 6-chloro-L-tryptophan, 6-methyl-DL-tryptophan, 7-methyl-DL-tryptophan, DL-7-azatryptophan, 5-azido-pentanoic acid, 2-Amino-N-(3-azidopropyl)-3-mercaptopropionamide, 2-Amino-N-(3-azidopropyl)-3-mercaptopropionamide, Azidohomoalanine, L-propargylglycine·DCHA, azidolysine, p-azidophenylalanine, Azidohomoalanine, D-propargylglycine, L-propargylglycine, azidolysine, Tris[(1-benzyl-1H-1,2,3-triazol-4-yl)methyl]amine, 2-(7'-octenyl) alanine, 2-(4'-pentenyl) alanine, 2-(4'-pentenyl)glycine, 2-(7'-octenyl) alanine, [5-((2-Aminoethyl)amino)naphthalene-1-sulfonic acid], L-glutamic acid-γ-[2-(1-sulfonyl-5-naphthyl)-aminoethylamine], N—ε-(5-carboxyfluorescein)-L-lysine, N—ε-(5/6-carboxyfluorescein)-L-lysine, N—ε-(4,4-dimethylazobenzene-4'carbonyl)-L-lysine, NF-2,4-dinitrophenyl-L-lysine, N—ε-[(7-methoxycoumarin-4-yl)-acetyl-L-lysine, glycosylated amino acids (e.g., Ser(β-D-GlcNAc(Ac)3)—OH, Thr(β-D-GlcNAc(Ac)3)—OH), 3-azabicyclo[3.1.0]hexane-2-carboxylic acid, 4-amino-(1-carboxymethyl) piperidine, 4-phenylpiperidine-4-carboxylic acid, Nα-methyl-N-im-trityl-L-histidine, Nα-methyl-O-benzyl-L-serine dicyclohexylammonium salt, Nalpha-methyl-Nomega-(4-methoxy-2,3,6-trimethylbenzenesulfonyl)-L-arginine, Nalpha-methyl-L-leucine, Nalpha-methyl-L-norvaline, Nalpha-methyl-L-phenylalanine, Nalpha-methyl-N-im-trityl-L-histidine, Nalpha-methyl-O-t-butyl-L-serine, Nalpha-methylglycine, 21-amino-4,7,10,13,16,19-hexaoxaheneicosanoic acid, {2-[2-(amino)-ethoxy]-ethoxy}acetic acid, 6-Amino-4-oxohexanoic acid, 5-Amino-3-Oxopentanoic Acid, NH—(PEG)10-CH2CH2COOH, NH—(PEG)12-CH2CH2COOH, 9-Amino-4; 7-Dioxanonanoic acid, 9-Amino-4; 7-Dioxanonanoic acid, 12-amino-4,7,10-trioxadodecanoic acid, 15-amino-4,7,10,13-tetraoxapentadecacanoic acid, 18-amino-4,7,10,13,16-pentaoxaoctadecanoic acid, 21-amino-4,7,10,13,16,19-hexaoxaheneicosanoic acid, NH—(PEG)8-CH2CH2COOH, 11-amino-3,6,9-trioxaundecanoic acid, N-(Fmoc-8-amino-3,6-dioxa-octyl)succinamic acid, —N—ε-acetyl-L-lysine, L-citrulline, Arg(Me)(Pbf)-OH, Nω,ω-dimethyl-L-arginine (asymmetrical and symmetrical), Lys(Me)2-OH chloride, N—ε,ε-t-methyl-L-lysine, Lys (Me3)-OH chloride, O-benzyl-L-phosphoserine, O-benzyl-D-phosphothreonine, O-benzyl-L-phosphothreonine, and O-benzyl-L-phosphotyrosine.

The side chain of the unnatural amino acid could be a side chain radical of a non-proteinogenic amino acid. The non-proteinogenic amino acid could, e.g., be ornithine or citrulline.

In the compounds of the invention, $R_1$, $R_2$ and X could each independently be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

Any of the compounds of Formulas (I), (IA), (IB), (IC), (II), (III), and (IV) listed above may comprise one or more of the following:

A is $NR_3R_4$, wherein $R_3$ is H and $R_4$ is tert-butoxycarbonyl, 9-fluorenylmethoxycarbonyl, 2-(3,5-dimethoxyphenyl)propan-2-yloxycarbonyl;

A is N-phthalimidyl;

A is $NR_3R_4$, $R_3$ is H, $R_4$ is tert-butoxycarbonyl, 9-fluorenylmethoxycarbonyl, 2-(3,5-dimethoxyphenyl)propan-2-yloxycarbonyl, and $R_3$ and $R_1$ are connected and together form a side chain radical of proline;

X is selected from the group consisting of imidazolyl and benzotriazolyl;

X is S-D; and D is an alkyl;

X is S-D; and D is an alkyl, wherein the alkyl is ethyl;

X is O-L; and L is imidazolyl or benzotriazolyl;

X is O-L; and L is imidazolyl;

X is O-L; and L is benzotriazolyl;

X is unsubstituted;

X is substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

$Z_1$ and $Z_2$ are both N;

$Z_1$ and $Z_2$ are both C;

$Z_1$ is N and $Z_2$ is C;

$Z_1$ is C and $Z_2$ is N;

$R_1$ and $R_2$ are both selected from a group consisting of side chain radicals of natural amino acids;

$R_1$ and $R_2$ are both selected from a group consisting of side chain radicals of an unnatural amino acid;

$R_1$ is selected from a group consisting of side chain radicals of natural amino acids, and $R_2$ is selected from a group consisting of side chain radicals of an unnatural amino acids;

$R_2$ is selected from a group consisting of side chain radicals of natural amino acids, and $R_1$ is selected from a group consisting of side chain radicals of an unnatural amino acids;

$R_1$ and $R_2$ are both unsubstituted;

$R_1$ is substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

$R_2$ is substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

$R_1$ is unsubstituted and $R_2$ is substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

$R_2$ is unsubstituted and $R_1$ is substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

$R_1$ is a side chain radical of a non-proteinogenic amino acid;

$R_2$ a side chain radical of a non-proteinogenic amino acid;

$R_1$ and $R_2$ is each independently a side chain radical of a non-proteinogenic amino acid;

Both $R_1$ and $R_2$ are independently substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

The compounds of Formulas (I), (IA), (IB), (IC), (II), (III), and (IV) listed above may be prepared using the methods described in U.S. Ser. No. 16/869,692, filed on May 8, 2020, U.S. Ser. No. 16/869,749, filed on May 8, 2020, and U.S. Ser. No. 16/869,794, filed on May 8, 2020, all three hereby incorporated by reference.

The invention is further directed to the use of compounds of Formulas (I), (IA), (IB), (IC), (II), (III), and (IV) in the preparation of compounds of Formula (V):

(V)

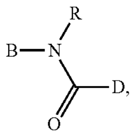

wherein

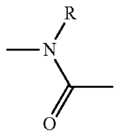

is at the N-terminus and/or the C-terminus, and/or covalently bound to the N-terminus and/or the C-terminus, or at or adjacent to a cleavage or a hydrolysis site of the compound of Formula (V);

wherein B is selected from the group consisting of hydrogen, —$NH_2$, —$NNH_2$, —$CONH_2$, —$COOR_3$, —COOH, —COH, —$COC_1$—$C_4$ alkyl, —$COC_1$—$C_4$ haloalkyl, —OH, an amino acid, an aza amino acid, a 2 to 60-mer peptide, a 2 to 60-mer aza peptide, a 2 to 60-mer azatide;

D is selected from the group consisting of —$OR_4$, —OH, —$NH_2$, —$NNH_2$, —$NHCOCH_3$, —$NHCH_3$, —$N(CH_3)_2$, —$CONH_2$, —COOH, —COH, —$COC_1$—$C_4$ alkyl, —$COC_1$—$C_4$ haloalkyl, an amino acid, an aza amino acid, a 2 to 60-mer peptide, a 2 to 60-mer aza peptide, a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.) Compounds of Formula (V) are azapeptide analogues of compounds of Formula (VI):

(VI)

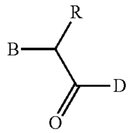

wherein B is selected from the group consisting of hydrogen, —$NH_2$, —$NNH_2$, —$CONH_2$, —$COOR_3$, —COOH, —COH, —$COC_1$—$C_4$ alkyl, —$COC_1$—$C_4$ haloalkyl, —OH, an amino acid, an aza amino acid, a 2 to 60-mer peptide, a 2 to 60-mer aza peptide, a 2 to 60-mer azatide;

D is selected from the group consisting of —$OR_4$, —OH, —$NH_2$, —$NNH_2$, —$NHCOCH_3$, —$NHCH_3$, —$N(CH_3)_2$, —$CONH_2$, —COOH, —COH, —$COC_1$—

$C_4$ alkyl, —$COC_1$—$C_4$ haloalkyl, an amino acid, an aza amino acid, a 2 to 60-mer peptide, a 2 to 60-mer aza peptide, and a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In the preferred embodiments, compounds of Formula (V) are more resistant to hydrolysis and/or enzymatic degradation than compounds of Formula (VI). In some of these preferred embodiments, compounds of Formula (V) are more potent than compounds of Formula (VI), e.g., due to a better fit into a biological receptor. Compounds of Formula (V) could be used, e.g., in drug discovery, diagnosis, prevention and treatment of diseases.

The invention is further directed to the use of compounds of Formulas (I), (IA), (IB), (IC), (II), (III), and (IV) in the preparation of compounds of Formula (V):

(V)

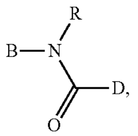

wherein

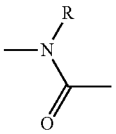

is adjacent to the N-terminus and/or the C-terminus of the compound of Formula (V);

wherein B is selected from the group consisting of hydrogen, —$NH_2$, —$NNH_2$, —$CONH_2$, —$COOR_3$, —COOH, —COH, —$COC_1$—$C_4$ alkyl, —$COC_1$—$C_4$ haloalkyl, —OH, an amino acid, an aza amino acid, a 2 to 60-mer peptide, a 2 to 60-mer aza peptide, a 2 to 60-mer azatide;

D is selected from the group consisting of —$OR_4$, —OH, —$NH_2$, —$NNH_2$, —$NHCOCH_3$, —$NHCH_3$, —$N(CH_3)_2$, —$CONH_2$, —COOH, —COH, —$COC_1$—$C_4$ alkyl, —$COC_1$—$C_4$ haloalkyl, an amino acid, an aza amino acid, a 2 to 60-mer peptide, a 2 to 60-mer aza peptide, a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.) Compounds of Formula (V) are azapeptide analogues of compounds of Formula (VI):

(VI)

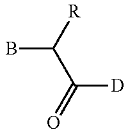

wherein B is selected from the group consisting of hydrogen, —$NH_2$, —$NNH_2$, —$CONH_2$, —$COOR_3$, —COOH, —COH, —$COC_1$—$C_4$ alkyl, —$COC_1$—$C_4$ haloalkyl, —OH, an amino acid, an aza amino acid, a 2 to 60-mer peptide, a 2 to 60-mer aza peptide, a 2 to 60-mer azatide;

D is selected from the group consisting of —$OR_4$, —OH, —$NH_2$, —$NNH_2$, —$NHCOCH_3$, —$NHCH_3$, —$N(CH_3)_2$, —$CONH_2$, —COOH, —COH, —$COC_1$—$C_4$ alkyl, —$COC_1$—$C_4$ haloalkyl, an amino acid, an aza amino acid, a 2 to 60-mer peptide, a 2 to 60-mer aza peptide, a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.);

R is selected from the group consisting of side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, serine, threonine, cysteine and glutamine may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.). In the preferred embodiments, compounds of Formula (V) are more resistant to hydrolysis and/or enzymatic degradation than compounds of Formula (VI). In some of these preferred embodiments, compounds of Formula (V) are more potent than compounds of Formula (VI), e.g., due to a better fit into a biological receptor. Compounds of Formula (V) could be used, e.g., in drug discovery, diagnosis, prevention, inhibition, and treatment of diseases.

In certain embodiments, in compounds of Formula (V) and compounds of Formula (VI), B of each compound is independently selected from the group consisting of hydrogen, —$NH_2$, —$NNH_2$, —$CONH_2$, —$COOR_3$, —$COC_1$—$C_4$ alkyl, —$COC_1$—$C_4$ haloalkyl, —OH, an amino acid, an aza amino acid, a 2 to 60-mer peptide, a 2 to 60-mer aza peptide, a 2 to 60-mer azatide;

D of each compound is independently selected from the group consisting of —$OR_4$, —$NH_2$, —$NNH_2$, —$NHCOCH_3$, —$NHCH_3$, —$N(CH_3)_2$, —$CONH_2$, —COOH, —COH, —$COC_1$—$C_4$ alkyl, —$COC_1$—$C_4$ haloalkyl, an amino acid, an aza amino acid, a 2 to 60-mer peptide, a 2 to 60-mer aza peptide, a 2 to 60-mer azatide;

$R_3$ and $R_4$ is each independently selected from the group consisting of $C_1$-$C_6$ alkyl (e.g., methyl), methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.); and R of each compound is independently selected from the group consisting of side chain radicals of aspartic acid, phenylalanine, alanine, histidine, glutamic acid, tryptophan, valine, leucine, lysine, serine, threonine, methionine, tyrosine, isoleucine (including, R-isoleucine, S-isoleucine and RS-isoleucine), arginine, glycine, asparagine, and glutamine. The side chain radical of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, may be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.) or a protecting group (e.g., Phth, Boc, Fmoc, Ddz, etc.).

The invention is further directed to the use of compounds of Formulas (I), (IA), (IB), (IC), (II), (III), and (IV) in the preparation of azabradykinin, including, e.g., aza-7 bradykinin, aza-2,8 bradykinin, aza-2 bradykinin, and aza-8 bradykinin:

aza-7 bradykinin

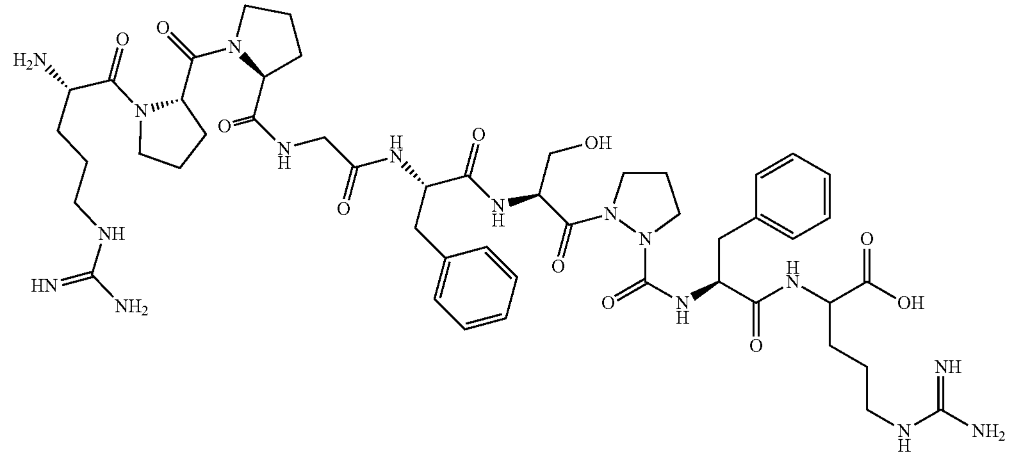

aza-2,8 bradykinin

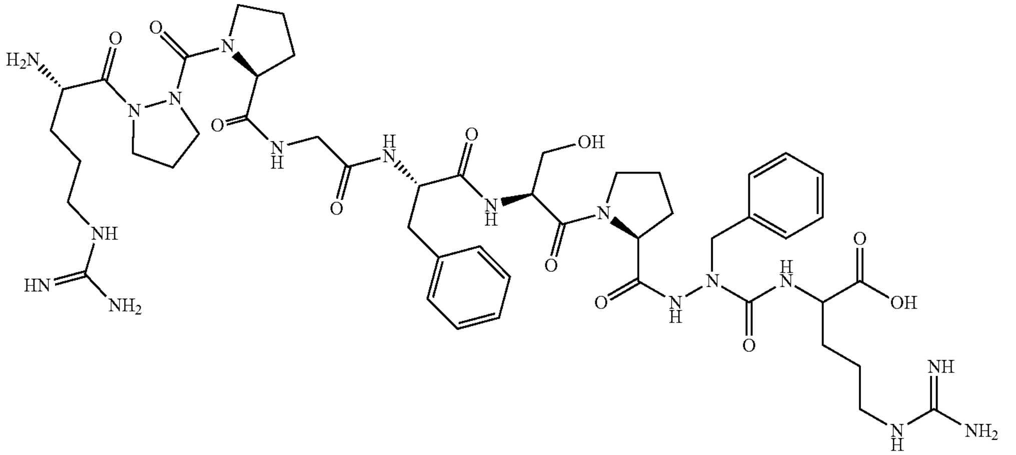

-continued aza-2 bradykinin

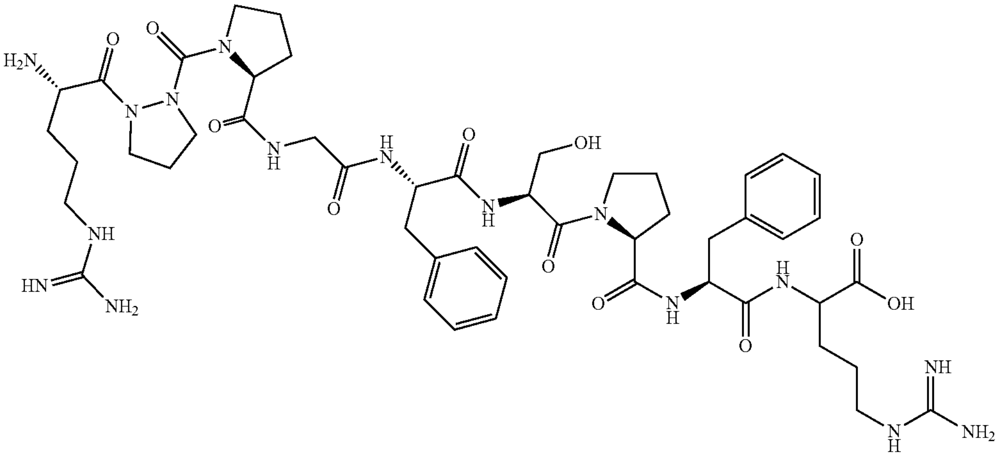

aza-8 bradykinin

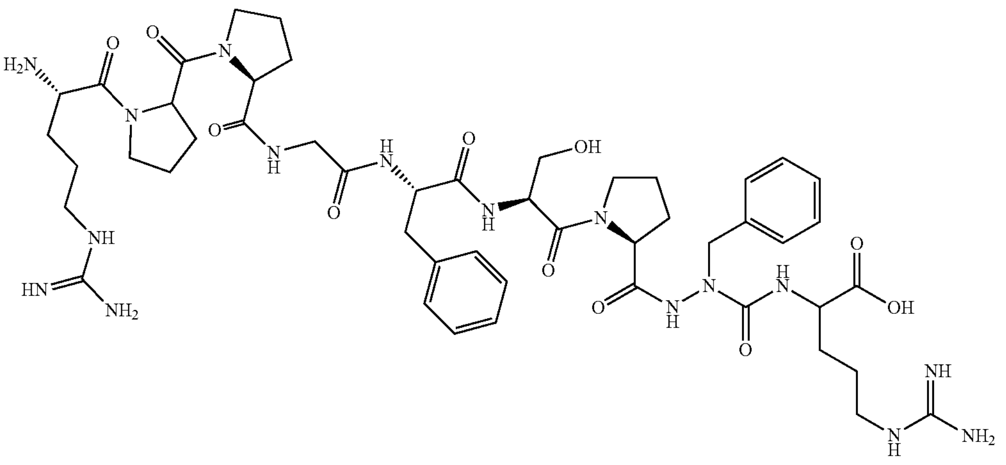

The invention is further directed to the use of dimers (e.g., di-azatides) described in U.S. Ser. No. 16/869,692, filed on May 8, 2020, U.S. Ser. No. 16/869,749, filed on May 8, 2020, and U.S. Ser. No. 16/869,794, filed on May 8, 2020, all three hereby incorporated by reference in their entireties, in preparation of azapeptides and other peptidomimetic agents.

The invention is also directed in part to a method of preparing a compound of Formula (V), the method comprising a step of activating a compound of Formula (I), Formula (IA), Formula (IB), Formula (IC), Formula (II), Formula (III) or Formula (IV) to form an activated compound of Formula (I), Formula (II), Formula (III), or Formula (IV), a step of coupling the activated compound of Formula (I), Formula (IA), Formula (IB), Formula (IC), Formula (II), Formula (III), or Formula (IV) with N-terminal of an amino acid, N-terminal of an aza-mino acid, provided that, if a side chain of the amino acid or aza-amino acid contains a group selected from amino, amide, guanidino N, carboxyl, sulfhydryl, carboxyl, hydroxyl, indole, imidazole phenol, the group is protected with a protecting group selected from tert-butoxycarbonyl, 9-fluorenylmethoxycarbonyl, or 2-(3,5-dimethoxyphenyl)propan-2-yloxycarbonyl, phthalimide, carboxybenzyl, 2,2,4,6,7-pentamethyl-dihydrobenzofuran-5-sulfonyl, trityl or triphenylmethyl, t-butyl ester, t-butyl ether, S-t-butyl ether, allyloxycarbonyl, methoxytrimethylbenzene sulfonyl, 4,4-dimethyloxybenzhydryl, 2,2,5,7,8-pentamethyl-chroman-6-sulfonyl chloride, 2,4,6-trimethoxybenzyl, allyl ester, acetamidomethyl (Acm), and the like to form a protected compound of Formula (V), and a step of deprotecting the protected compound of Formula (V). In certain embodiments, compound of Formula (V) is deprotected, e.g., with hydrazine, piperadine, TFA, acetic acid, thioanisole, EDT, anisole, etc., to form the compound of Formula (V).

In certain embodiments, compounds of Formula (I), Formula (IB), Formula (IC), Formula (II), Formula (III), and Formula (IV) are activated by iodomethane (MeI). For example, in certain embodiments, the compound of Formula (IA), Formula (IB), Formula (IC), Formula (II), or Formula (III) is a phthalimide-protected carbamoyl imidazole and is activated, e.g., by MeI.

In certain embodiments, the compounds of Formula (I), Formula (IB), Formula (IC), Formula (II), Formula (III), Formula (IV) are activated, e.g., by DIPEA in acetonitrile. For example, in certain embodiments, the compound of Formula (IA), Formula (IB), Formula (IC), Formula (II) or Formula (III) is phthalimide-protected carbamoyl benzotriazole and is activated by DIPEA in acetonitrile.

The invention is also directed in part to the compounds of Formula (VII):

(VII)

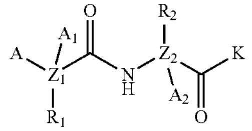

and salts thereof, wherein

A is N-phthalimidyl or $NR_3R_4$, wherein $R_3$ is H and $R_4$ is tert-butoxycarbonyl, 9-fluorenylmethoxycarbonyl, 2-(3,5-dimethoxyphenyl)propan-2-yloxycarbonyl, or $R_3$ and $R_1$ are connected and together form a side chain radical of proline;

$A_1$ is hydrogen or absent;

$A_2$ is hydrogen or absent;

K is a halogen;

$R_1$ and $R_2$ is each independently selected from the group consisting of side chain radicals of natural amino acid and side chain radicals unnatural amino acid amino acids;

$Z_1$ and $Z_2$ is each independently C or N.

The invention is also directed in part to the compounds of Formula (VII):

(VII)

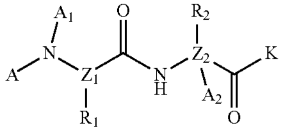

and salts thereof, wherein

A is tert-butoxycarbonyl, 9-fluorenylmethoxycarbonyl, 2-(3,5-dimethoxyphenyl)propan-2-yloxycarbonyl;

$A_1$ is H or absent;

$A_2$ is H or absent;

K is a halogen;

$R_1$ and $R_2$ is each independently selected from the group consisting of side chain radicals of natural amino acid and side chain radicals unnatural amino acid amino acids;

$Z_1$ and $Z_2$ is each independently C or N.

The invention is also directed in part to the compounds of Formula (VII):

(VII)

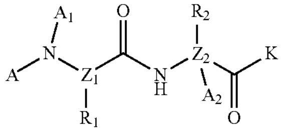

and salts thereof, wherein $A_1$ is absent or H,

A is tert-butoxycarbonyl, 9-fluorenylmethoxycarbonyl, 2-(3,5-dimethoxyphenyl)propan-2-yloxycarbonyl;

K is a halogen;

$R_1$ and $R_2$ is each independently selected from the group consisting of side chain radicals of natural amino acid and side chain radicals unnatural amino acid amino acids;

$Z_1$ and $Z_2$ is each independently C or N, and at least one of $Z_1$ and $Z_2$ is N.

In certain embodiments, compounds of Formula (VII) are stable compounds formed during azapeptide synthesis from the dimers of the invention, e.g., by an activation of compounds of Formula (I), Formula (IB), Formula (IC), Formula (II), Formula (III) and Formula (IV), wherein, X is S-D, and D is selected from the group consisting of alkyls, aryls and heteroaryls. In certain embodiments, compounds of Formula (VII) could be coupled, e.g., with N-terminal of an amino acid, N-terminal of an aza-mino acid, N-terminal of a compound according to Formula (I), Formula (IB), Formula (IC), Formula (II), Formula (III), Formula (IV), Formula (V), or Formula (VI).

The invention is also directed in part to compounds of Formula (IV), wherein A is tert-butoxycarbonyl or 9-fluorenylmethoxycarbonyl; X is Cl; $R_1$ and $R_2$ is each independently selected from the group consisting of side chain radicals of aspartic acid, phenylalanine, alanine, histidine, glutamic acid, tryptophan, valine, leucine, lysine, serine, threonine, methionine, tyrosine, isoleucine (including, R-isoleucine, S-isoleucine and RS-isoleucine), arginine, glycine, asparagine, and glutamine; $Z_1$ and $Z_2$ is each independently C or N, and at least one of $Z_1$ and $Z_2$ is N.

In certain embodiments, compounds of Formula (I), Formula (IA), Formula (IB), Formula (IC), Formula (II), Formula (III) and Formula may be activated, e.g., by halonium reagents (e.g., trichloroisocyanuric acid ("TCCA"), or a combination of tetrabutyl ammonium chloride ("TBACl") with tetrabutyl ammonium chloride ("TBACl")). TBACl enhances reaction performance when added prior to TCCA. These milder conditions and temperatures are compatible with, e.g., the protecting groups that are commonly used in the synthesis of amino acids, aza-amino acids, aza-amino acid conjugates, peptides, azapeptides, and side chains of conventional amino acids.

In certain embodiments, compounds of Formula (I), Formula (IA), Formula (IB), Formula (IC), Formula (II), Formula (III) and Formula may be activated, e.g., with TCCA and TBCl to form a compound according Formula (VII), and coupling the activated compound with an amine. The amine could be selected from the group consisting of amino esters, esters of amino acids, amino esters of aza-amino acids, peptides, and aza-peptides. The reaction may be performed, e.g., in chloroform, dichloromethane, or acetone. In some embodiments, from about 0.5 to about 2 equivalents of TCCA and TBCl are used. In some embodiments, from about 1 to about 3 equivalents of the amine are used. In some embodiments, from about 1.1 to about 1.8 equivalents of TCCA and TBCl, and from about 1.0 to about 1.5 equivalents of the amine are used. The coupling may, e.g., be for a time period of from 15 minutes to 12 hours. In certain embodiments, the coupling may be completed in about 30 minutes, about 40 minutes, about 50 minutes, about 60 minutes, about 70 minutes, about 80 minutes, about 90 minutes, about 100 minutes, about 110 minutes, or about 120 minutes. In certain embodiments, acetonitrile is used as a solvent both during the activating and coupling steps. In certain embodiments, dimethylformamide is used as a solvent during the coupling step.

In an additional aspect, the invention is directed to a process for synthesizing azapeptides (e.g., by solution phase synthesis), the method comprising activating a dimer with TCCA and TBCl to form a reactive acyl chloride, and coupling the reactive acyl chloride with an amine, wherein the dimer is a compound according to any one of Formulas (I)-(IV), the reactive amine chloride is a compound according to Formulas (VII), and the amine is selected from the group consisting of amino esters, esters of amino acids, amino esters of aza-amino acids, peptides, and aza-peptides. In some of these embodiments, the amine is a peptide or an aza-peptide. In some embodiments, the azapeptide is a compound according to Formula (V).

In certain embodiments, the invention is also directed to a process for a systematic insertion of an aza-amino acid or an aza-amino acid segment(s) at a desired position(s) along the peptide sequence comprising activating a dimer with TCCA and TBCl to form in situ a reactive acyl chloride, and coupling the reactive chloride with an amine, wherein the dimer is a compound according to any one of Formulas (I)-(IV), and the reactive amine chloride is a compound according to Formula (XI). The amine could be selected, e.g., from the group consisting of amino esters, esters of amino acids, amino esters of aza-amino acids, peptides, and aza-peptides. In some embodiments, the amine is a compound according to Formula (V).

The invention is also directed to a method of preparing an azapeptide comprising a step of activating a compound according to Formula (I), Formula (IA), Formula (IB), Formula (IC), Formula (II), Formula (III) or Formula (IV); and a step of coupling the activated compound with N-terminal of an amino acid, N-terminal of an aza-mino acid; wherein the azapeptide is a compound of Formula (V). The compound of Formula (I), Formula (IA), Formula (IB), Formula (IC), Formula (II), Formula (III) or Formula (IV) may be unsubstituted or substituted with one or more of the following: a halogen, a $C_1$-$C_6$ alkyl, hydroxyl, —COOH, —COH, methoxyl, ethoxyl, propoxyl, or a $C_1$-$C_6$ haloalkyl. The

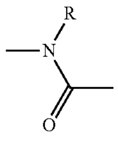

in the compound of Formula (V) may be at the N-terminus and/or the C-terminus of the compound of Formula (V), adjacent to the N-terminus and/or the C-terminus of the compound of Formula (V), or at a hydrolysis site of the compound of Formula (V). In some embodiments, the compound of Formula (I), Formula (IA), Formula (IB), Formula (IC), Formula (II), Formula (III), or Formula (IV) is activated by iodomethane; the coupling is in acetonitrile and comprises addition of DIPEA; and is during a solid phase azapeptide synthesis. In additional embodiments, the compound of Formula (I), Formula (IA), Formula (IB), Formula (IC), Formula (II), Formula (III) or Formula (IV) is activated by iodomethane, the coupling is in acetonitrile and comprises addition of DIPEA, and is during a liquid phase azapeptide synthesis.

In the methods of the invention, the azapeptide is preferably prepared in a yield of at least about 40% (by weight) (e.g., from about 45% to about 65%, from about 50% to about 65%, or from about 55% to about 65%, etc.). In certain embodiments, the yield is greater than about 45%, about 50%, about 55%, or about 60%. Thus, the yield may, e.g., be about about 50%, about 55%, about 60%, or about 65%. In certain embodiments, the azapeptide is a di-azapeptide and is synthesized in a yield from about 80% to about 98%. However, in other embodiments, the azapeptide may be prepared in a yield of from about 5% to less than about 40% (e.g., about 36%).

In certain embodiments, the invention is also directed in part to a method of preparing a compound of Formula (V), the method comprising a step of coupling a first compound of Formula (I), (IA), (IB), (IC), (II), (III), or (IV) with an amino acid, a second compound of Formula (I), (IA), (IB), (IC), (II), (III), or (IV), a peptide, or an azatide in acetonitrile at a temperature from 15° C. to 35° C., wherein the coupling is for a time period from about 15 minutes to about 24 hours, from about 15 minutes to about 20 hours, from about 15 minutes to about 18 hours, from about 20 minutes to about 16 hours, from about 20 minutes to about 14 hours, from about 20 minutes to about 12 hours, from about 20 minutes to about 10 hours, from about 20 minutes to about 8 hours, from about 20 minutes to about 6 hours, from about 30 minutes to about 5 hours, from about 40 minutes to about 4 hours, from about 50 minutes to about 3 hours, from about 50 minutes to about 2 hours. In some of these embodiments, the coupling is for a time period from about 30 minutes to about 90 minutes at a temperature from about 18° C. to about 25° C. From about 1 to about 3 equivalents of DIPEA and from about 1 equivalents to about 1.4 equivalents (preferably, about 1.1 equivalent) of the amino acid, the second compound of Formula (I), (IA), (IB), (IC), (II), (III), or (IV), the peptide, or the azatide may be added to the acetonitrile for the coupling reaction. In some embodiments, no additional reagents are added during the coupling step.

In certain embodiments, a compound that is being coupled is an azapeptides with activated carbamoyl imidazole moiety, and about 1.5 eq of an amino acid and about 1.0 eq of DIPEA are used, and the coupling is at room temperature under nitrogen for about 20 hours. In certain embodiments, a compound that is being coupled is an azatide with activated carbamoyl imidazole moiety, and about 1.5 eq hydrazines and about 1.0 eq DIPEA are used, and the coupling is at about 40° C. under nitrogen for about 20 hours.

In certain embodiments, a compound that is being coupled is an azapeptide with carbamoyl benzotriazole (HBt) moiety, and about 1.5 eq. of an amino acid and about 2.0 eq. of DIPEA are used, and the coupling is at about 40° C. under nitrogen for about 20 hours.

In certain embodiments, a compound that is being coupled is an azapeptide with carbamoyl 1-O-benzotriazole (HOBt) moiety, and about 1.1 eq. of an amino acid and about 2.0 eq DIPEA are used, and the coupling is at about 25° C. under nitrogen for 1 hour.

In certain embodiments, the invention is also directed in part to a method of preparing a compound of Formula (V), the method comprising activating a compound of Formula (I), Formula (IA), Formula (IB), Formula (IC), Formula (II), Formula (III) or Formula (IV) to form an activated compound of Formula (I), Formula (IA), Formula (IB), Formula (IC), Formula (II), Formula (III), or Formula (IV), and coupling the activated compound of Formula (I), Formula (IA), Formula (IB), Formula (IC), Formula (II), Formula (III), or Formula (IV) with N-terminal of an amino acid, N-terminal of an aza-mino acid, provided that, if a side chain of the amino acid or aza-amino acid contains a group selected from amino, amide, guanidino N, carboxyl, sulfhydryl, carboxyl, hydroxyl, indole, imidazole phenol, the group is protected with a protecting group selected from tert-butoxycarbonyl, 9-fluorenylmethoxycarbonyl, or 2-(3,5-dimethoxyphenyl)propan-2-yloxycarbonyl, phthalimide, carboxybenzyl, 2,2,4,6,7-pentamethyl-dihydrobenzofuran-5-sulfonyl, trityl or triphenylmethyl, t-butyl ester, t-butyl ether, s-t-butyl ether, allyloxycarbonyl, methoxytrimethylbenzene sulfonyl, 4,4-dimethyloxybenzhydryl, 2,2,5,7,8- pentamethyl-chroman-6-sulfonyl chloride, 2,4,6-trimethoxybenzyl, allyl ester acetamidomethyl, and the like to form a protected compound of Formula (V), and deprotecting the protected compound of Formula (V), e.g., with hydrazine, piperadine, TFA, acetic acid, thioanisole, EDT, anisole, etc., to form the compound of Formula (V).

The invention is further directed in part to a solution phase synthesis of the compounds of Formula (V), the solution phase synthesis comprising a step of converting a compound of Formula (I), (IA), (IB), (IC), (II), (III), or (IV) to an amide of the compound of Formula (I), (IA), (IB), (IC), (II), (III), or (IV), a step of deprotecting the amide of the compound of Formula (I), (IA), (IB), (IC), (II), (III), or (IV), a step of coupling the deprotected amide of Formula (I), (IA), (IB), (IC), (II), (III), or (IV) with an additional compound of Formula (I), (IA), (IB), (IC), (II), (III), or (IV), or a protected amino acid, or a protected aza-amino acid to form a protected azapeptide, and a step of deprotecting the protected azapeptide to provide a compound of Formula (V).

In certain embodiments, the invention is directed in part to a solid phase synthesis of the compounds of Formula (V), the solid phase synthesis comprising a step of coupling a protected compound of Formula (I), (IA), (IB), (IC), (II), (III), or (IV) to a support, a step of deprotecting the protected compound of Formula (I), (IA), (IB), (IC), (II), (III), or (IV), a step of coupling the deprotected compound of Formula (I), (IA), (IB), (IC), (II), (III), or (IV) to an additional protected compound of Formula (I), (IA), (IB), (IC), (II), (III), or (IV), an additional protected amino acid, or an additional protected aza-amino acid to form a protected peptide, and a step of deprotecting and cleaving the protected peptide to provide a compound of Formula (V).

In certain embodiments, the invention is also directed in part to a process of preparing a compound of Formula (V) comprising a step of cleaving a peptide at its N-terminus and/or C-terminus, and a step of coupling the cleaved peptide with a compound of Formula (I), (IA), (IB), (IC), (II), (III), or (IV) to form a compound of Formula (V). In certain embodiments, the compound of Formula (I), (IA), (IB), (IC), (II), (III), or (IV) is activated prior to the coupling with the cleaved peptide.

The invention is also directed in part to a process of preparing a compound of Formula (V) comprising a step of cleaving a peptide at its cleavage site to form two smaller peptides, a step of replacing the last amino acid of at least one of the smaller peptides with an aza-amino acid to form an azapeptide, and a step of conjugating the azapeptide with the remaining smaller peptide to provide a compound of Formula (V).

The invention is also directed in part to a process of preparing a compound of Formula (V) comprising hydrolizing a peptide at its cleavage site, and reacting the cleaved peptide with a compound of Formula (I), (IA), (IB), (IC), (II), (III), or (IV) to provide a compound of Formula (V).

The invention is further directed in part to a method of azapeptide synthesis comprising reacting a compound of Formula (I), (IA), (IB), (IC), (II), (III), or (IV) with an aza-amino acid, an amino acid, or a peptide to form the azapeptide, wherein the azapeptide is a compound of formula (V).

The compounds of Formula (I), (IA), (IB), (IC), (II), (III), or (IV) and process of the invention allow, e.g., for preparation of a compound of Formula (V) in yields (% by weight) of at least about 40% (e.g., from about 45% to about 65%, from about 50% to about 65%, or from about 55% to about 65%, etc.). In certain embodiments, the yield is greater than about 45%, about 50%, about 55%, or about 60%. Thus, the yield may, e.g., be about 50%, about 55%, about 60%, or about 65%. However, in certain other embodiments, compounds of Formula (V) may be prepared in smaller yields (e.g., from about 5% to about 355).

The invention is further directed in part to prolonging an in vitro and/or in vivo half-life of a peptide, comprising synthesizing a peptidomimetic analogue of the peptide with the compounds of Formula (I), (IA), (IB), (IC), (II), (III) or (IV), the peptidomimetic analogue containing an aza amino acid instead of amino acid at the N-terminus of the peptide, but is otherwise identical to the peptide. In certain embodiments, the peptidomimetic analogue is a compound of Formula (V) or (VI), and is synthesized by liquid phase or solid phase chemistry. In certain embodiments, liquid phase chemistry may be preferred.

The invention is also directed in part to a process of preparing a compound of Formula (V) comprising cleaving a peptide at its cleavage site to form two smaller peptides, replacing the last amino acid of at least one of the smaller peptides with a compound according to any one of Formulas (I)-(IV) to form an azapeptide, and conjugating the azapeptide with the remaining smaller peptide to provide a compound of Formula (V).

The invention is also directed in part to a process of preparing a compound of Formula (V) comprising hydrolizing a peptide at its cleavage site, and reacting the cleaved peptide with a compound according to any one of Formulas (I)-(IV) to provide a compound of Formula (V).

The invention is further directed in part to a method of an azapeptide synthesis comprising reacting a compound according to any one of Formulas (I)-(IV) with an aza-amino acid, an amino acid, a peptide, an azapeptide, or an additional compound according to any one of Formulas (I)-(IV) to form an azapeptide. The azapeptide may be, e.g., a compound of Formula (V).

In certain embodiments, the invention is further directed in part to a solid phase synthesis of an azapeptide, the solid phase synthesis comprising coupling a compound according to any one of Formulas (I)-(IV) to a support, and coupling an additional protected compound according to any one of Formulas (I)-(IV), an additional protected amino acid, or an additional protected aza-amino acid to the deprotected compound of according to any one of Formulas (I)-(IV). In certain embodiments, the compound according to any one of Formulas (I)-(IV) may be deprotected prior to said coupling.

In certain embodiments, the invention is further directed in part to a solid phase synthesis of an azapeptide, the solid phase synthesis comprising coupling a compound according to any one of Formulas (I)-(IV) to a support, deprotecting the compound according to any one of Formulas (I)-(XII), and coupling the deprotected compound of according to any one of Formulas (I)-(XII) to a protected compound according to any one of Formulas (I)-(IV), a protected amino acid, or an a protected aza-amino acid.

In certain embodiments, the invention is further directed in part to a solution phase synthesis of a compound according to Formula (V), the solution phase synthesis comprising deprotecting a compound of any one of Formulas (I)-(IV), and coupling the deprotected compound with an additional compound any one of Formulas (I)-(IV), or a protected amino acid, or a protected aza-amino acid to form a protected azapeptide. The synthesis may further comprise a step of deprotecting the protected azapeptide to provide a compound of Formula (V). The coupling may, e.g., be for a time period of from about 15 minutes to about 12 hours. In certain embodiments, the coupling may be completed in about 30 minutes, about 40 minutes, about 50 minutes, about 60 minutes, about 70 minutes, about 80 minutes, about 90 minutes, about 100 minutes, about 110 minutes, or about 120 minutes.

The invention is further directed in part to prolonging an in vitro and/or in vivo half-life of a peptide, comprising synthesizing a peptidomimetic analogue of the peptide with the compounds of Formula (I), (IA), (IB), (IC), (II), (III) or (IV), the peptidomimetic analogue containing an aza amino acid instead of amino acid at a position adjacent to the N-terminus of the peptide, but is otherwise identical to the peptide. In certain embodiments, the peptidomimetic analogue is a compound of Formula (V) or (VI), and is synthesized by a liquid phase or a solid phase chemistry.

The invention is further directed in part to the use of compounds of Formula (V) and Formula (VI) in prevention, diagnosis, inhibition and treatment of medical conditions, including, e.g., cardiovascular disorders, CNS disorders, neurodegenerative disorders, immune system disorders, metabolic disorders, fertility, dental conditions, pain, inflammation, dermatological conditions, blood disorders, infection, eye disorders, gynecologic disorders, urologic disorders, bone and connective tissue disorders, respiratory disorders, gastrointestinal disorders, disorders of endocrine system, and cancer.

The methods of diagnosing, prevention and treatment of medical conditions in accordance with the present invention comprise administering a therapeutically effective amount of a compound of Formula (V) or Formula (VI) to a subject in need thereof at specific times in a pharmaceutically acceptable formulation.

Definitions

The term "about" in the present specification means a value within 15% (±15%) of the value recited immediately after the term "about," including the value equal to the upper limit (i.e., +15%) and the value equal to the lower limit (i.e., −15%) of this range. For example, the phrase "about 100" encompasses any numeric value that is between 85 and 115, including 85 and 115.

An "azapeptide" means a peptide in which one or more α-carbon(s) are replaced by nitrogen trivalent atom(s).

An "azatide" means a peptide in which all α-carbons are replaced by nitrogen trivalent atoms.

An "aza-amino acid" is defined as an amino acid where the chiral α-carbon atom is replaced by a nitrogen atom.

An "α-nitrogen" means a nitrogen atom bonded to a carbonyl group in an azapeptide or an azatide. The carbon atom next to the α-nitrogen is called the β-carbon.

An "azapeptide analogue" means a compound which differs from a peptide that it is an analogue of in that one or more α-carbon atoms of the peptide have been replaced by a nitrogen atom with or without additional structural modification(s) to the side chain(s) of the amino acid residues of the peptide. The one or more α-carbon atoms that are replaced may, e.g., be at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide). Despite having a backbone different from the peptide, the azapeptide analogue preserves, extends and/or improves functional activity of the peptide. The azapeptide analogue is more resistant to degradation than the peptide and/or has an improved therapeutic activity than the peptide and/or has an improved selectivity for a biological receptor than the peptide and/or improved affinity to a biological receptor and/or reversed activity at a biological receptor (agonistic activity instead of antagonist activity or antagonistic activity instead of agonistic activity).

The term "heteroaryl" includes all aryl compounds with atoms other than C and H.

The term "protected" as it is used herein means that one or more group(s) (e.g., —OH) in an amino acid, an aza-amino acid, a peptide, an azapeptide, or a compound is protected with a protecting group (e.g., Phth, Ddz, etc.). Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups include, for example, nitrogen protecting groups and hydroxy-protecting groups. Examples of protective group include, e.g., benzyl, diphenylmethyl, trityl, Cbz, Boc, Fmoc, methoxycarbonyl, ethoxycarbonyl, Phth, Ddz, as well as other protective groups known to those skilled in the art.

A "side chain radical" of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, and glutamine have the following structures:

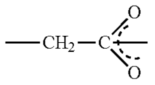

Aspartic Acid

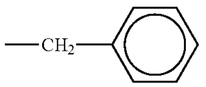

Phenylalanine $—CH_3$

Alanine

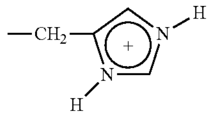

Histidine

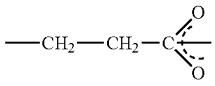

Glutamic Acid

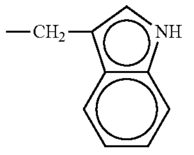

Tryptophan

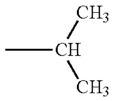

Valine

-continued

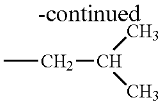

Leucine $—CH_2—CH_2—CH_2—CH_2—NH_3^+$

Lysine $—CH_2—CH_2—S—CH_3$

Methionine

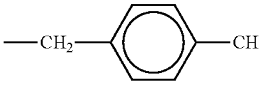

Tyrosine

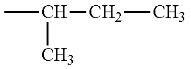

Isoleucine

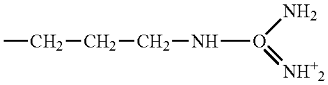

Arginine

—H

Glycine

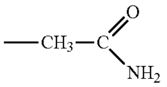

Asparagine

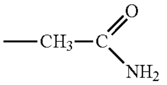

Glutamine

A "side chain radical of proline" is a secondary amine, in that the alpha-amino group is attached directly to the main chain, making the α carbon a direct substituent of the side chain:

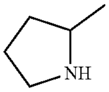

Amino acids which may be used in the present invention are L- and D-amino acids.

Unless otherwise indicated, the terms "prevent," "preventing" and "prevention" contemplate an action that occurs before a patient begins to suffer from the symptoms of specified disease or disorder, which inhibits or reduces the severity of the disease or disorder or of one or more of its symptoms. The terms encompass prophylaxis.

The compounds of the invention may be used in the form of pharmaceutically acceptable salts derived from inorganic or organic acids. For clarity, the term "pharmaceutically acceptable salt[s]" as used herein generally refers to salts prepared from pharmaceutically acceptable acids or bases including inorganic acids and bases and organic acids and bases. Suitable pharmaceutically acceptable base addition salts include, e.g., metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific acids include, e.g., hydrochloric, hydrobromic, phosphoric, sulfuric, and methanesulfonic acids. Examples of specific salts include, e.g., hydrochloride and mesylate salts. Others are well-known in the art. See, e.g., Remington's Pharmaceutical Sciences, 18th ed. (Mack Publishing, Easton Pa.: 1990) and Remington: The Science and Practice of Pharmacy, 19th ed. (Mack Publishing, Easton Pa.: 1995). The preparation and use of acid addition salts, carboxylate salts, amino acid addition salts, and zwitterion salts of compounds of the present invention may also be considered pharmaceutically acceptable if they are, within the scope of sound medical judgment, suitable for use in contact with the tissues of humans and lower animals without undue toxicity, irritation, allergic response, and the like, are commensurate with a reasonable benefit/risk ratio, and are effective for their intended use. Such salts may also include various solvates and hydrates of the compound of the present invention.

Certain compounds of the present invention may be isotopically labelled, e.g., with various isotopes of carbon, fluorine, or iodine, as applicable when the compound in question contains at least one such atom. In preferred embodiments, methods of diagnosis of the present invention comprise administration of such an isotopically labelled compound.

Certain compounds of the present invention may exist as stereoisomers wherein, asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Certain compounds of the present invention may exist as cis- or trans isomers, wherein substituents on a ring may attach in such a manner that they are on the same side of the ring (cis) relative to each other, or on opposite sides of the ring relative to each other (trans). Such methods are well known to those of ordinary skill in the art, and may include separation of isomers by recrystallization or chromatography. It should be understood that the compounds of the invention may possess tautomeric forms, as well as geometric isomers, and that these also constitute an aspect of the invention.

Unless otherwise indicated, a "diagnostically effective amount" of a compound is an amount sufficient to diagnose a disease or condition. In general, administration of a compound for diagnostic purposes does not continue for as long as a therapeutic use of a compound, and could be administered only once if such is sufficient to produce the diagnosis.

The term "Phth-protected carbamoyl aza-imidazole derivative of an unnatural amino acid" as used herein means an unnatural aza-amino acid covalently bound (conjugated) to phthalimidyl at its N-terminus and to imidazole at its C-terminus. The unnatural amino acid may be substituted and unsubstituted.

The term "Phth-protected carbamoyl aza-benzotriazole derivative of an unnatural amino acid" as used herein means an unnatural aza-amino acid covalently bound (conjugated) to phthalimidyl at its N-terminus and to benzotriazole at its C-terminus. The unnatural amino acid may be substituted and unsubstituted.

The term "solid-phase synthesis" means a method in which molecules (e.g., amino acids, aza-amino acids, etc.) are covalently bound on a solid support material and synthesised step-by-step in a single reaction vessel utilising selective protecting group chemistry. In this method, building blocks are typically protected at all reactive functional groups. The order of functional group reactions may be controlled by the order of deprotection. For example, in an aza-peptide synthesis, an amino-protected amino acid or an amino-protected aza-amino acid is bound to a solid phase material (e.g., low cross-linked polystyrene beads), forming a covalent bond between the carbonyl group and the resin, e.g., an amido or an ester bond. Then, the amino group is deprotected and reacted with the carbonyl group of the next amino-protected amino acid or amino-protected aza-amino acid. This cycle is repeated to form the desired peptide or aza-peptide chain. After all reactions are complete, the synthesised peptide or aza-peptide is cleaved from the bead.

The terms "solution phase synthesis" and "liquid phase synthesis" means a method in which molecules (e.g., amino acids, aza-amino acids, etc.) are synthesized in a solution without being covalently bound on a solid support material.

The term "synthon" means a building block.

The term "room temperature" means 20° C.

The term "ambient temperature" means 18-28° C.

The terms "parent peptide" and "corresponding peptide" mean a native peptide (i.e., natural or convention peptide) that differs from an azapeptide in that one or more of the amino residue(s) of the native peptide is (are) replaced by a semicarbazide or a substituted semicarbazide (i.e., one or more α-carbon(s) of the native peptide are replaced by nitrogen trivalent atom(s)) in the azapeptide. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

The term "phthalimidyl" means:

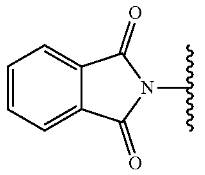 [SMILES: *N1C(=O)c2ccccc2C1=O]

The term "phthaloyl" means:

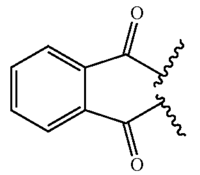 [SMILES: *C(=O)c1ccccc1C(*)=O]

The abbreviation "N-Phth" means "N-phthalimidyl."

The abbreviation "Boc" means "tert-butoxycarbonyl."

The abbreviation "Fmoc" means "9-fluorenylmethoxycarbonyl."

The abbreviation "Ddz" means "2-(3,5-dimethoxyphenyl) propan-2-yloxycarbonyl."

The abbreviation "HOBt" means "1-OH-Benzotriazole."

The abbreviation "SPPS" means "Solid Phase Peptide Synthesis."

The abbreviation "TCCA" means "trichloroisocyanuric acid."

The abbreviation "TBACl" means "tetrabutyl ammonium chloride."

The abbreviation "Phth" means "phthaloyl."

The abbreviation "Cbz" means "carboxybenzyl."

The abbreviation "Pbf" means "2,2,4,6,7-pentamethyl-dihydrobenzofuran-5-sulfonyl."

The abbreviation "Trt" means "trityl or triphenylmethyl."

The abbreviation "OtBu" means "O-t-butyl."

The abbreviation "tBu" means "t-butyl."

The abbreviation "StBu" means S-t-butyl ether.

The abbreviation "Aloc" means "allyloxycarbonyl."

The abbreviation "Mtr" means "methoxytrimethylbenzene sulfonyl."

The abbreviation "Mbh" means "4,4-dimethyloxybenzhydryl."

The abbreviation "Pmc" means "2,2,5,7,8-pentamethylchroman-6-sulfonyl chloride."

The abbreviation "Tmob" means 2,4,6-trimethoxybenzyl.

The abbreviation "OAI" means "allyl ester."

The abbreviation "Acm" means "acetamidomethyl."

The abbreviation "DEAD" means "Diethyl Azodicarboxylate" (IUPAC name N-ethyl-N-propan-2-ylpropan-2-amine).

In peptide chemistry, "deprotection" refers to a process of removing the protecting groups (e.g., phthaloyl, Boc, Cbz, Fmoc, etc) by a chemical agent. For example, Boc protecting group could be removed under acidic conditions (e.g., 4 M HCl, or neat trifluoroacetic acid TFA); Fmoc protecting group could be removed under basic conditions when pH is higher than 12 (20% pipyridine/DMF or DCM); and Phthaloyl group may be cleaved, e.g., under basic conditions or by the use of hydrazine.

DETAILED DESCRIPTION

A replacement of one or more α-carbon(s) with nitrogen in a peptide converts the peptide to an "azapeptide"; and replacement of all α-carbon(s) with nitrogen(s) in a peptide converts the peptide to an "azatide."

Azapeptides and azatides are peptidomimetics and are generally more resistant to enzymatic hydrolysis than corresponding peptides. The increase in resistance to enzymatic degradation may lead to increased metabolic stability of the compounds and/or an improved receptor binding (e.g., an improved affinity to the receptor). Therefore, azapeptides and azatides are useful tools for drug design, applications in medicinal chemistry, and in diagnosis, prevention and treatment of diseases, and may be used, e.g., instead of peptides, as azapeptide analogues ("peptidomimetics").

Compounds of Formula (I), (IA), (IB), (IC), (II), (III), and (IV) of the present invention could be used as "building blocks" or synthons for the synthesis of azapeptides and other peptidomimetics and aza-amino acid conjugates, including compounds of Formula (V) in a solution phase synthesis, a solid phase synthesis or a synthesis comprising both a solution phase synthesis and a solid phase synthesis. In certain embodiments, solution phase synthesis is preferred.

Preparation of Compounds of Formula (I), (IA), (IB), (IC), (II), (III) and (IV)

Compounds of Formula (I), (IA), (IB), (IC), (II), (III), and (IV) may be prepared, e.g., by the methods described in U.S. Ser. No. 16/869,692, filed on May 8, 2020, U.S. Ser. No. 16/869,749, filed on May 8, 2020, and U.S. Ser. No. 16/869,794, filed on May 8, 2020, all three hereby incorporated by reference in their entireties.

Synthesis of Azapeptides and Azatides

Compounds of Formula (I), (IA), (IB), (IC), (II), (III), and (IV) may be coupled in a linear, stepwise, chain-lengthening fashion to each other, amino acids, aza-amino acids, peptides, azapeptides, and azatides by solution or liquid phase, solid-phase and mixed solution/solid phase synthetic methodologies to construct compounds of Formulas (V). In some of these embodiments, preparation by solution phase synthetic methodologies is preferred.

Compounds of Formula (I), (IA), (IB), (IC), (II), (III), and (IV) can also be used, e.g., as sub-units to elongate and/or cap peptides and azapeptides.

For example, in certain embodiments, compounds of Formula (I), (IA), (IB), (IC), (II), (III), and (IV) may be activated by iodomethane, and the activated compound may be coupled, e.g., a protected or unprotected aza-amino acid; a protected or unprotected peptide; a protected or unprotected azapeptide; a protected or unprotected azatide; or a protected or unprotected compound of Formula (I), Formula (IA), Formula (IB), Formula (IC), Formula (II), Formula (III), or Formula (IV); or a protected or unprotected hydrazine, by either solution or liquid phase synthetic methodologies, e.g., to form a compound of Formula (V). The amino acid, the aza-amino acid, the peptide, the azapeptide, compound of Formula (I), (IA), (IB), (IC), (II), (III), and (IV) may each be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.). The coupling may, e.g., be for up to about 20 hours. In certain embodiments, the coupling may be completed in about 30 minutes, about 40 minutes, about 50 minutes, about 60 minutes, about 70 minutes, about 80 minutes, about 90 minutes, about 100 minutes, about 110 minutes, or about 120 minutes.

In certain embodiments, compounds of Formula (I), (IA), (IB), (IC), (II), (III), and (IV) may be activated by methylation of imidazole residue using MeI, and the activated compound may be coupled, e.g., a protected or unprotected aza-amino acid; a protected or unprotected a peptide; a protected or unprotected azapeptide; a protected or unprotected azatide; or a protected or unprotected compound of Formula (I), Formula (IA), Formula (IB), Formula (IC), Formula (II), Formula (III), or Formula (IV); or a protected or unprotected hydrazine, by either solution or liquid phase synthetic methodologies, e.g., to form a compound of Formula (V) or Formula (VII). The amino acid, the aza-amino acid, the peptide, the azapeptide, compound of Formula (I), (IA), (IB), (IC), (II), (III), and (IV) may each be unsubstituted or substituted with one or more of the following: a halogen (Cl, F, or Br), a $C_1$-$C_6$ alkyl (e.g., methyl), hydroxyl, —COOH, —COH, methoxyl, ethoxyl, propoxyl, a $C_1$-$C_6$ haloalkyl (e.g., a chloromethyl, a fluromethyl, etc.). The methylation of imidazole residue could, e.g., in acetonitrile at 25° C. under nitrogen for 20 hours.

The methods of the invention may be used to synthesize azapeptides and azatides from 3 to 200 mers in length, e.g., tri-azatides, tetra-azapeptides, penta-azapeptides, etc. In certain embodiments, the peptide is 9 mers in length.

In certain embodiments, the method of preparing an azapeptide or an azatide comprises hydrolysing a peptide, e.g., a compound of Formula (VI) into fragments and reacting one or more fragments with a compound of Formula (I), (IA), (IB), (IC), (II), (III), or (VI).

In certain embodiments, the method of preparing an azapeptide or an azatide comprises cleaving a peptide, e.g., a compound of Formula (VI), into fragments and reacting one or more fragments with a compound of Formula (I), (IA), (IB), (IC), (II), (III), or (VI).

In certain embodiments, the method of preparing an azapeptide or an azatide comprises cleaving an end of a peptide, e.g., a compound of Formula (IV), and reacting the cleaved peptide with a compound of Formula (I), (IA), (IB), (IC), (II), (III), or (VI).

In certain embodiments, the method of preparing an azapeptide or an azatide comprises reacting a compound of Formula (I), (IA), (IB), (IC), (II), (III), or (VI) with a truncated peptide.

In certain embodiments, the method of preparing an azapeptide or an azatide comprises conjugating a compound of Formula (I), (IA), (IB), (IC), (II), (III), or (VI) with a truncated peptide, e.g., a compound of Formula (V).

In certain embodiments, a method of azapeptide or azatide synthesis comprises reacting (i) a benzotriazole derivative of an aza-amino acid comprising an aza-amino acid covalently bound (conjugated) to a protecting group at its N-terminus and to benzotriazole at its C-terminus with (ii) a peptide to form the azapeptide or azatide, wherein the benzotriazole derivative of the aza-amino acid azapeptide or azatide is a compound of Formula (I), (IA), (IB), (IC), (II) or (III).

In certain embodiments, a method of azapeptide or azatide synthesis comprises reacting (i) an imidazole derivative of an aza-amino acid comprising an aza-amino acid covalently bound (conjugated) to a protecting group at its N-terminus and to imidazole at its C-terminus, wherein the aza-amino acid is selected from the group consisting of aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, and aza-arginine with (ii) a hydrazide to form an azapeptide. In certain embodiments, the imidazole derivative is a compound of Formula (I).

Compounds of Formula (I), (IA), (IB), (IC), (II), (III), and (IV) may be used in the methods of azapeptide and azatide syntheses described in U.S. Ser. No. 16/869,692, filed on May 8, 2020, U.S. Ser. No. 16/869,749, filed on May 8, 2020, and U.S. Ser. No. 16/869,794, filed on May 8, 2020, in preparation of azapeptides and other peptidomimetic agents, instead of or with the building blocks described in these applications. The disclosure of U.S. Ser. No. 16/869,692, filed on May 8, 2020, U.S. Ser. No. 16/869,749, filed on May 8, 2020, and U.S. Ser. No. 16/869,794, filed on May 8, 2020, and specifically the reactions, conditions and reactants disclosed in these three applications are all hereby incorporated by reference in their entireties.

Uses of Compounds of Formula (V)

Compounds of Formula (V) are azapeptide analogues of compounds of Formula (VI). In the preferred embodiments, compounds of Formula (V) are more resistant to hydrolysis and/or enzymatic degradation than compounds of Formula (VI).

Compounds of Formula (V) may be used to inhibit peptidases, both in vitro and in vivo. The peptidase may, e.g., be an endopeptidase, an exopeptidase, an aspartic protease, a glutamic protease, an asparagine peptide lyase, or a retroviral protease.

In some of these preferred embodiments, compounds of Formula (V) are more potent than compounds of Formula (VI), e.g., due to a better fit into a biological receptor. Compounds of Formula (V) could be used, e.g., in drug discovery, diagnosis, prevention, inhibition, and treatment of diseases.

Compounds of Formulas (V) may each comprise from 3 to 200 carbonyl group(s). For example, compounds of Formula (V) may each comprise 4, 5, 6, 7, 8, 9, 10, 11, 12, 13, 14, 15, 16, 17, 18, 19, 20, 22, 23, 24, 25, 26, 27, 28, 29, 30, 31, 32, 33, 34, 36, 37, 38, 39, 40, 41, 43, 44, 56, or 166 carbonyl groups. In certain embodiments, compounds of Formula (V) comprise from 3 to 60 carbonyl groups, from 3 to 50 carbonyl groups, from 3 to 40 carbonyl groups, from 3 to 30 carbonyl groups, from 3 to 25 carbonyl groups, from 3 to 20 carbonyl groups, from 3 to 15 carbonyl groups, from 3 to 12 carbonyl groups, from 3 to 10 carbonyl groups, from 3 to 9 carbonyl groups, from 4 to 40 carbonyl groups, from 4 to 30 carbonyl groups, from 4 to 25 carbonyl groups, from 4 to 20 carbonyl groups, from 4 to 15 carbonyl groups, from 4 to 12 carbonyl groups, from 4 to 10 carbonyl groups, or from 4 to 9 carbonyl groups.

In certain embodiments, compounds of Formula (V) comprise from 3 to 200 carbonyl groups and at least one α-nitrogen covalently bound to at least one of said carbonyl groups, and have a greater bioavailability (e.g., oral, transdermal, and/or intranasal) than a peptide structurally different from the compounds of Formula (V) only in that that the peptide comprises α-carbon instead of said α-nitrogen. In certain embodiments, the α-nitrogen is at the N-termini or C-termini of the compounds of Formula (V). In certain embodiments, the α-nitrogen is at the N-termini and the C-termini of the compounds of Formula (V). In certain embodiments, the α-nitrogen is not at the N-termini and not at the C-termini of the compounds of Formula (V), rather it is at a cleavage or hydrolysis site(s) of the peptide.

In certain embodiments, compounds of Formula (V) are azapeptide analogues of therapeutic peptides.

In certain embodiments, compounds of Formula (V) are azapeptide analogues of diagnostic peptides.

Compounds of Formula (V) may be used in drug discovery, diagnosis, prevention, inhibition, and treatment of diseases.

In certain embodiments, compounds of Formula (V) comprise a backbone comprising from 2 to 200 carbonyl groups and α-nitrogen covalently bound to at least one of said carbonyl groups, and are therapeutically effective for the treatment of a disorder in a subject, while a peptide structurally different from the compounds of Formula (V) only in that that the peptide comprises α-carbon instead of said α-nitrogen is not therapeutically effective for the treatment of the disorder. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 3 to 200 carbonyl groups and α-nitrogen covalently bound to at least one of said carbonyl groups, and have a therapeutic efficacy greater than a peptide structurally different from the compounds of Formula (V) only in that the peptide comprises an α-carbon instead of said α-nitrogen. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 3 to 200 carbonyl groups and α-nitrogen covalently bound to at least one of said carbonyl groups, and have a longer duration of therapeutic activity than a peptide structurally different from the compounds of Formula (V) only in that that the peptide comprises α-carbon instead of said α-nitrogen. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 3 to 75 carbonyl groups and at least one α-nitrogen covalently bound to at least one of said carbonyl groups, and have an in vivo half-life greater than a peptide structurally different from the compounds of Formula (V) only in that said at least one α-nitrogen is replaced with α-carbon. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise a backbone comprising from 2 to 75 carbonyl groups, wherein at least two carbonyl groups are covalently bound to a trivalent nitrogen, and compounds of Formula (V) have an in vivo half-life greater than a peptide structurally different from the compounds of Formula (V) only in that one or more alpha nitrogen(s) of the compounds of Formula (V) is replaced with alpha carbon(s). The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise at least one aza-amino acid, and have an in vivo half-life greater than a peptide structurally different from the compounds of Formula (V) only in that the aza-amino acid(s) is replaced with a corresponding amino acid. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 3 to 200 carbonyl groups and α-nitrogen covalently bound to at least one of said carbonyl groups, and are more resistant to protease degradation than a peptide structurally different from the compounds of Formula (V) only in that that the peptide comprises α-carbon instead of said α-nitrogen. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprise from 3 to 200 carbonyl groups and α-nitrogen covalently bound to at least one of said carbonyl groups, and have a greater affinity to a biological receptor than a peptide structurally different from the compounds of Formula (V) only in that that the peptide comprises α-carbon instead of said α-nitrogen. The replacement may be, e.g., at the N-termini of the peptide (i.e., the first residue of the peptide), at the second residue of the peptide, the C-termini of the peptide (i.e., the last residue of the peptide), the residue covalently bound to the C-termini of the peptide, and/or at another residue of the peptide (e.g., at the site of hydrolysis of the peptide).

In certain embodiments, compounds of Formula (V) comprises from 3 to 60 carbonyl groups.

In certain embodiments, compounds of Formula (V) are linear.

In certain embodiments, compounds of Formula (V) are cyclic.

In certain embodiments, compounds of Formula (V) are pegylated.

In certain embodiments, compounds of Formula (V) are conjugated to an immunoglobulin.

In certain embodiments, compounds of Formula (V) comprise α-nitrogen at the N-terminus of its backbone.

In certain embodiments, compounds of Formula (V) comprise α-nitrogen at the C-terminus of its backbone In certain embodiments, compounds of Formula (V) comprise two carbonyl groups and two α-nitrogens.

In certain embodiments, compounds of Formula (V) comprise three carbonyl groups and one α-nitrogen.

In certain embodiments, compounds of Formula (V) comprise three carbonyl groups and two α-nitrogens.

In certain embodiments, compounds of Formula (V) comprise three carbonyl groups and three α-nitrogens.

In certain embodiments, compounds of Formula (V) comprise four carbonyl groups and one α-nitrogen.

In certain embodiments, compounds of Formula (V) comprise four carbonyl groups and two α-nitrogens.

In certain embodiments, compounds of Formula (V) comprise four carbonyl groups and three α-nitrogens.

In certain embodiments, compounds of Formula (V) comprise four carbonyl groups and four α-nitrogens.

In certain embodiments, compounds of Formula (V) are azapeptide analogues of a 3 to 200 amino acid peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 3 to 200 amino acid peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine, wherein the analogue includes at least one corresponding aza-amino acid of the amino acid.

In certain embodiments, compounds of Formula (V) are azapeptide analogues of a 3 to 200 amino acid peptide, the 3 to 200 amino acid peptide comprising amino acids selected from the group consisting of glycine, alanine, valine, leucine, isoleucine, proline, phenylalanine, tyrosine, tryptophan, aspartic acid, glutamic acid, aspargine, glutamine, histidine, lysine, arginine, the analogue differing from the amino acid peptide in that that the aza-analogues comprise an aza-amino acid instead of at least one of the amino acids, wherein the aza-analogues comprise aza-glycine instead of glycine, and/or the aza-analogues comprise aza-alanine instead of alanine, and/or the aza-analogues comprise aza-valine instead of valine, and/or the aza-analogues comprise aza-leucine instead of leucine, or/and the aza-analogues comprise aza-isoleucine instead of iso-leucine, and/or the aza-analogues comprise aza-proline instead of proline, and/or the aza-analogues comprise aza-phenylalanine instead of phenylalanine, or/and the aza-analogues comprise comprises aza-tyrosine instead of tyrosine, and/or the aza-analogues comprise aza-tryptophan instead of tryptophan, or/and the aza-analogues comprise aza-aspartic acid instead of aspartic acid, and/or the aza-analogues comprise aza-glutamic acid instead of glutamic acid, and/or the aza-analogues comprise aza-aspargine instead of aspargine, and/or the aza-analogues comprise aza-glutamine instead of glutamine, and/or the aza-analogues comprise aza-histidine instead of histidine, and/or the aza-analogues comprise aza-lysine instead of lysine, and/or the aza-analogues comprise aza-arginine instead of arginine.

In certain embodiments, compounds of Formula (V) are azapeptide analogues of a peptide comprising from 3 to 50 amino acids selected from the group consisting of glycine, alanine, valine, leucine, isoleucine, proline, phenylalanine, tyrosine, tryptophan, aspartic acid, glutamic acid, aspargine, glutamine, histidine, lysine, arginine, and at least 3, 4, 5, 6, 7, 8, 9 or 10 of the amino acids are replaced with corresponding aza-amino acids. In some of these embodiments, the replaced amino acid is the first amino acid of the peptide. In some of these embodiments, the replaced amino acid is the last amino acid of the peptide. In some of these embodiments, the first and the last amino acids of the peptide are both replaced with corresponding aza-amino acids.

In certain embodiments, compounds of Formula (V) are azapeptide analogues of a 10-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 9-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 8-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 7-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 6-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 5-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 5-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 4-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 3-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, compounds of Formula (V) are azapeptide analogues of a 3-mer peptide comprising an amino acid selected from the group consisting of glycine, alanine, valine, leucine, isoleucine, proline, phenylalanine, tyrosine, tryptophan, aspartic acid, glutamic acid, aspargine, glutamine, histidine, lysine, and arginine; the aza-analogues differing from the amino acid peptide in that that the amino acid of the peptide is replaced with a corresponding aza-amino acid.

In certain embodiments, the last amino acid of the peptide is selected from the group consisting of aspartic acid, phenylalanine, and arginine.

In certain embodiment, the first amino acid of the peptide is selected from the group consisting of tyrosine, phenylalanine, and arginine.

In certain embodiments, the first and the last amino acid of the peptide are the same.

In certain embodiments, the first and the last amino acids of the peptide are different.

In certain embodiments, compounds of Formula (V) are not azatides.

In certain embodiments, compounds of Formula (V) comprise an amino acid selected from the group consisting of cysteine, methionine, serine and threonine.

In certain embodiments, compounds of Formula (V) comprise at least one, at least two or at least three aza-glycine(s).

In certain embodiments, compounds of Formula (V) comprise at least one, at least two or at least three aza-alanine(s).

In certain embodiments, compounds of Formula (V) comprise at least one, at least two or at least three aza-valine (s).

In certain embodiments, compounds of Formula (V) comprise at least one, at least two or at least three aza-leucine(s).

In certain embodiments, compounds of Formula (V) comprise at least one, at least two or at least three aza-isoleucine(s).

In certain embodiments, compounds of Formula (V) comprise at least one, at least two or at least three aza-proline(s).

In certain embodiments, compounds of Formula (V) comprise at least one, at least two or at least three aza-phenylalanine(s).

In certain embodiments, compounds of Formula (V) comprise at least one, at least two or at least three aza-tyrosine(s).

In certain embodiments, compounds of Formula (V) comprise at least one, at least two or at least three aza-tryptophan(s).

In certain embodiments, compounds of Formula (V) comprise at least one, at least two or at least three aza-aspartic acid(s).

In certain embodiments, compounds of Formula (V) comprise at least one, at least two or at least three aza-glutamic acid(s).

In certain embodiments, compounds of Formula (V) comprise at least one, at least two or at least three aza-aspargine(s).

In certain embodiments, compounds of Formula (V) comprise at least one, at least two or at least three aza-glutamine(s).

In certain embodiments, compounds of Formula (V) comprise at least one, at least two or at least three aza-histidine(s).

In certain embodiments, compounds of Formula (V) comprise at least one, at least two or at least three aza-lysine (s).

In certain embodiments, compounds of Formula (V) comprise at least one, at least two or at least three aza-arginine(s).

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini.

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, and are aza-analogues of a therapeutic peptide, and have a greater bioavailability (e.g., oral, transdermal, and/or intranasal) than the therapeutic peptide (in its unaltered state).

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, and are aza-analogues of a therapeutic peptide, maintain the therapeutic efficacy of the therapeutic peptide and have an in vivo half-life greater than the in vivo half-life of the therapeutic peptide.

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and have a longer duration of therapeutic activity than the therapeutic peptide.

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and are more resistant to protease degradation than the therapeutic peptide.

In certain embodiments, compounds of Formula (V) comprise aza-glycine, aza-alanine, aza-valine, aza-leucine, aza-isoleucine, aza-proline, aza-phenylalanine, aza-tyrosine, aza-tryptophan, aza-aspartic acid, aza-glutamic acid, aza-aspargine, aza-glutamine, aza-histidine, aza-lysine, or aza-arginine on their N-termini and/or C-termini, are aza-analogues of a therapeutic peptide and have a greater affinity to a biological receptor than the therapeutic peptide.

Tri-Azatide

In certain embodiments, a compound of Formula (V) is a tri-azatide of Formula (X):

(X)

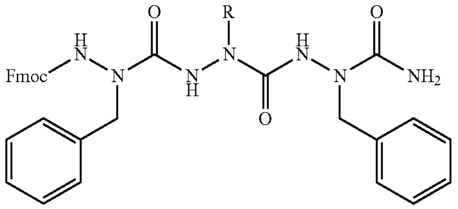

or a pharmaceutically acceptable salt thereof, wherein R is selected from the group consisting of unsubstituted and substituted side chain radicals of aspartic acid, phenylalanine, alanine, histidine, glutamic acid, tryptophan, valine, leucine, lysine, methionine, tyrosine, isoleucine (including, R-isoleucine, S-isoleucine and RS-isoleucine), arginine, glycine, asparagine, proline, and glutamine.

The tri-azatides may, e.g., be prepared by a solution phase or a solid phase synthesis.

The tri-azatides may be prepared both with C-to-N terminal construction and N-to-C terminal construction.

Tetra-Azapeptides

In certain embodiments, a compound of Formula (V) is a compound of formula:

K763

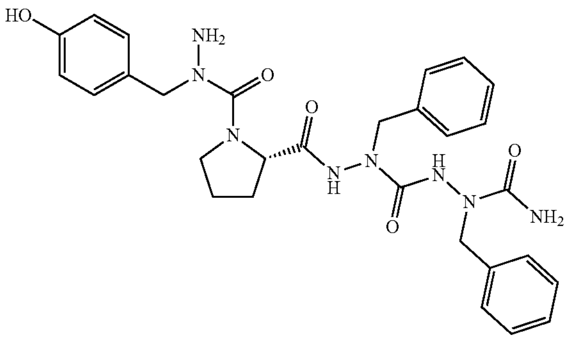

$C_{29}H_{34}N_8O_5$
Exact Mass: 574.27 or a pharmaceutically acceptable salt thereof.

In certain embodiments, a compound of Formula (V) is a compound of formula:

K883

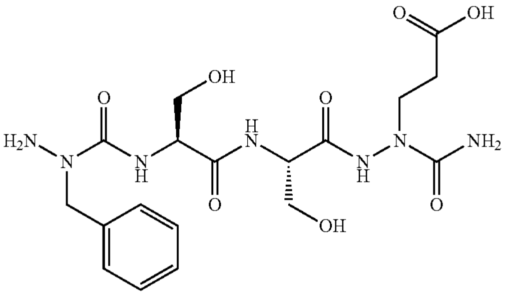

$C_{18}H_{27}N_7O_8$
Exact Mass: 469.19 or a pharmaceutically acceptable salt thereof.

The tetra-azatides may, e.g., be prepared by a solution phase or a solid phase synthesis.

The tetra-azatides may be prepared both with C-to-N terminal construction and N-to-C terminal construction.

Nine-Mer Azapeptides

In certain embodiments, a compound of Formula (V) is a compound of formula:

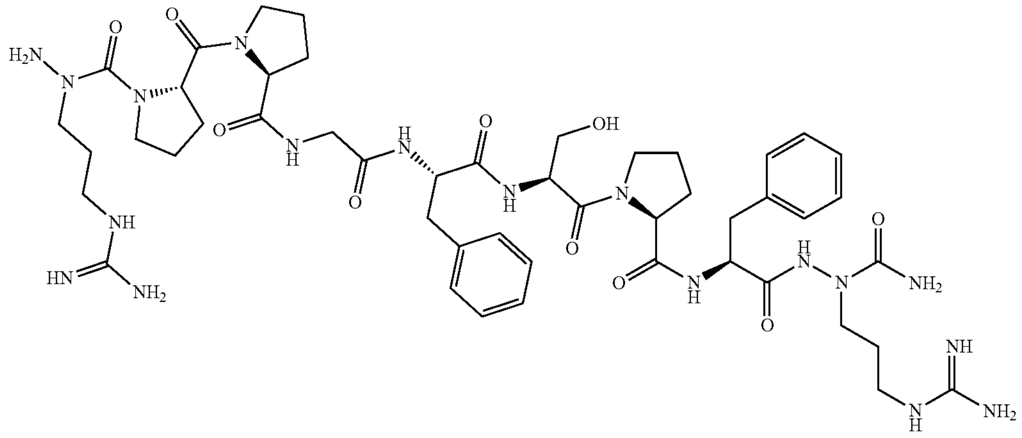 [SMILES: N=C(N)NCCCN(N)C(=O)N1CCC[C@H]1C(=O)N1CCC[C@H]1C(=O)NCC(=O)N[C@@H](Cc1ccccc1)C(=O)N[C@@H](CO)C(=O)N1CCC[C@H]1C(=O)N[C@@H](Cc1ccccc1)C(=O)NN(CCCNC(=N)N)C(N)=O]
or a pharmaceutically acceptable salt thereof.
In certain embodiments, a compound of Formula (V) is a compound of formula:
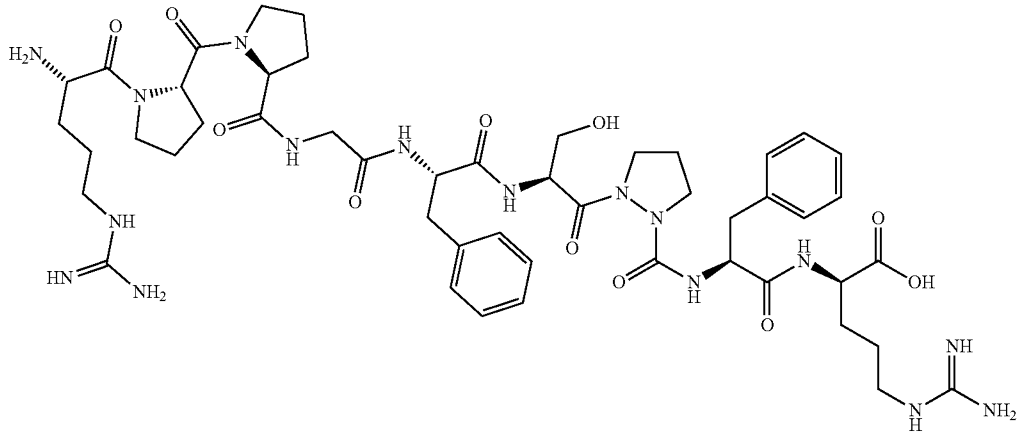 [SMILES: N=C(N)NCCC[C@H](N)C(=O)N1CCC[C@H]1C(=O)N1CCC[C@H]1C(=O)NCC(=O)N[C@@H](Cc1ccccc1)C(=O)N[C@@H](CO)C(=O)N1CCCN1C(=O)N[C@@H](Cc1ccccc1)C(=O)N[C@H](CCCNC(=N)N)C(=O)O]
or a pharmaceutically acceptable salt thereof.
In certain embodiments, a compound of Formula (V) is a compound of formula:
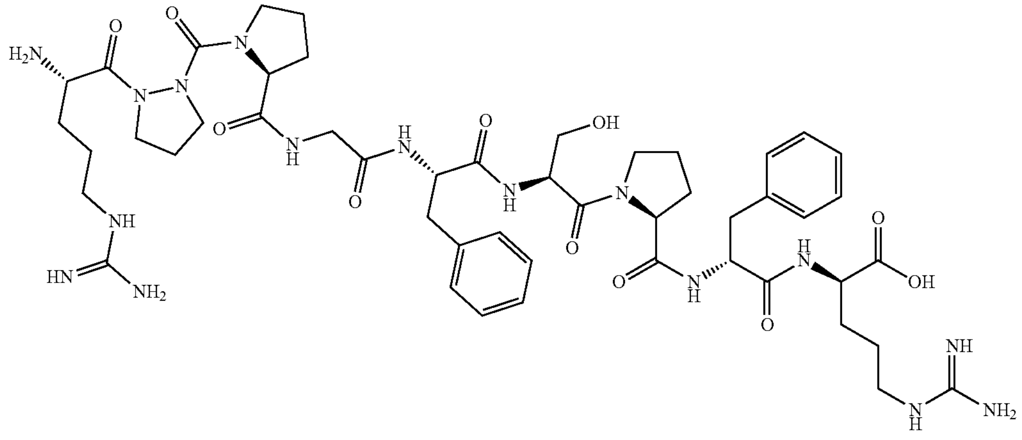 [SMILES: N=C(N)NCCC[C@H](N)C(=O)N1CCCN1C(=O)N1CCC[C@H]1C(=O)NCC(=O)N[C@@H](Cc1ccccc1)C(=O)N[C@@H](CO)C(=O)N1CCC[C@H]1C(=O)N[C@H](Cc1ccccc1)C(=O)N[C@H](CCCNC(=N)N)C(=O)O]
or a pharmaceutically acceptable salt thereof.

In certain embodiments, a compound of Formula (V) is a compound of formula:

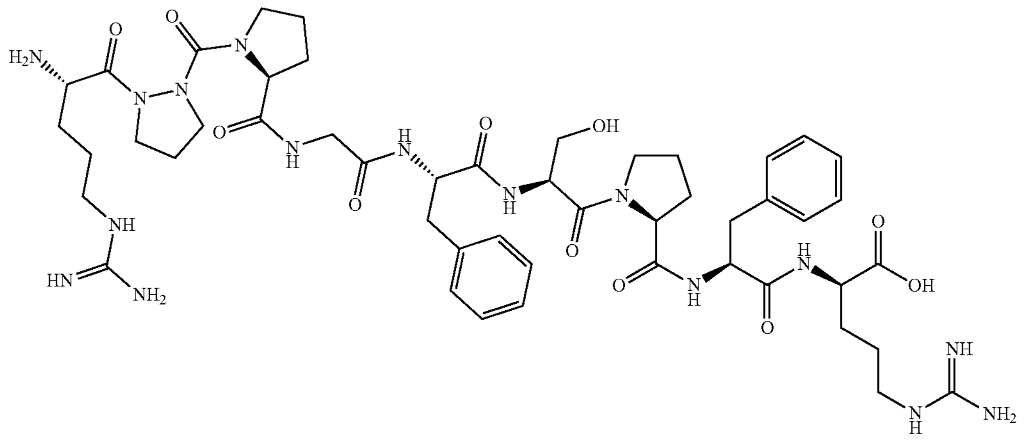 [SMILES: N=C(N)NCCC[C@H](N)C(=O)N1CCCN1C(=O)N1CCC[C@H]1C(=O)NCC(=O)N[C@@H](Cc1ccccc1)C(=O)N[C@@H](CO)C(=O)N1CCC[C@H]1C(=O)N[C@@H](Cc1ccccc1)C(=O)N[C@H](CCCNC(=N)N)C(=O)O]

or a pharmaceutically acceptable salt thereof.

In certain embodiments, a compound of Formula (V) is a compound of formula:

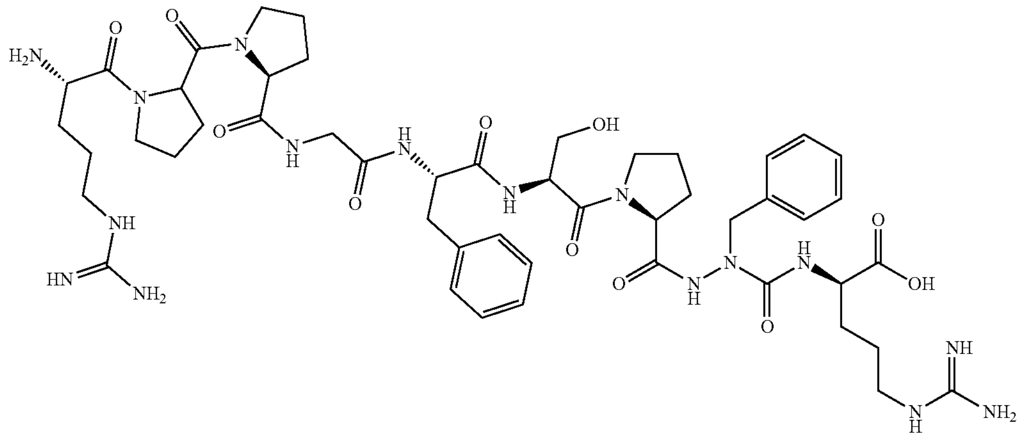 [SMILES: N=C(N)NCCC[C@H](N)C(=O)N1CCCC1C(=O)N1CCC[C@H]1C(=O)NCC(=O)N[C@@H](Cc1ccccc1)C(=O)N[C@@H](CO)C(=O)N1CCC[C@H]1C(=O)NN(Cc1ccccc1)C(=O)N[C@H](CCCNC(=N)N)C(=O)O]

or a pharmaceutically acceptable salt thereof.

The nine-mer azapeptides may, e.g., be prepared by a solution phase, a solid phase synthesis and a combination of the solution and solid phase synthesis.

The nine-mer azapeptides may be prepared both with C-to-N terminal construction and N-to-C terminal construction.

Additional Azapeptides

In certain embodiments, compounds of Formula (V) are selected from the group consisting of aza-analogues of A-6, A-623 (AMG-623), A-71378, A-75998, Abarelix (PPI-149), ABT-510, AC-100, AC-162352 (PYY 3-36), AC-253, AC-2592, AC-625, ACV-1, ADH-1, AEZS-108 (AN-152) (ZEN-008), AF-37702, Afamelanotide (EP-1647) (CUV-1647) (Melanotan I), AG2/102, AG-284, AI-502, AKL-0707 (LAB GHRH), Albiglutide (GSK-716155), Albuvirtide, ALG-889, Alloferon, Allotrap 2702 (B-2702), ALTY-0601, ALX-40-4C, Ambamustine (PTT-119), Anaritide, Antagonist G (PTL-68001), AOD-9604, APL-180, ATN-161, Atosiban (ORF-22164), Atriopeptin, Aviptadil (PSD-510), Avorelin (EP-23904), AZD-2315, Azetirelin (YM-14673), AZX-100, B27PD, BA-058, Barusiban (FE-200400), BAY-73-7977, BDM-E, BGC-728, BIM-23190, BIM-44002, BIO-1211, Bivalirudin (BG-8865), BMS-686117, Bremelanotide (PT-141), BRX-0585, Buserelin, Calcitonin (Human), Calcitonin (Salmon), Carbetocin, Carfilzomib (PR-171), Cargutocin (Y-5350), Carperitide (SUN-4936), Casokefamide, CB-182804, CB-183315, CBP-501, CBT-101, CCK (25-33), CD-NP, Cemadotin (LU-103793), Cetrorelix (NS-75), CG-77X56, CGRP (LAB-CGRP), Chlorotoxin (TM-601), Cilengitide (EMD-121974) (EMD-85189), CJC-1008 (DAC: Dynorphin A), CJC-1131 (DAC: GLP-1), CJC-1134 (PC-DAC) (Exendin-4), CJC-1295 (DAC:GRF), Cnsnqic-Cyclic (802-2), Compstatin (POT-4), Conantokin G, Contulakin G (CGX-1007), Corticorelin (NEU-3002), CP-95253, C-peptide (SPM-933), CR-665, CR-845, CTCE-0214, CTCE-9908, CTS-21166 (ASP-1702) (ATG-Z1) (OM-00-3) (OM-99-2), CVX-045, CVX-060, CVX-096 (PF-4856883), CZEN-002, D-4F (APP-018), Danegaptide (ZP-1609) (WAY-261134) (GAP-134), Davalintide (AC-2307), Davunetide (AL-108) (AL-208), Degarelix (FE 200486), Delmitide (RDP-58), Deltibant (CP-0127), Deslorelin, Desmopressin, Detirelix (RS-68439), DG-3173 (PTR-3173), Didemnin B (NSC-325319), Dirucotide (MBP-8298) Disitertide (NAFB-001) (P-144), DMP-728 (DU-728), dnaJP1 (AT-001), Dopastatin (BIM-23A760), DPK-060, DRF-7295, DSC-127, Dynorphin A, E-2078, EA-230, Ebiratide (Hoe-427), Edotreotide (SMT-487), Edratide (TV-4710), Efegatran (LY-294468), Elcatonin, Eledoisin (ELD- 950), Elisidepsin (PM-02734), EMD-73495, Enfuvirtide (T-20), EP-100, EP-51216 (EP-51389), Eptifibatide (C68-22), ET-642 (RLT-peptide), ETRX 101, Examorelin (EP-23905) (MF-6003), Exenatide (AC-2993) (LY-2148568), Exsulin (INGAP Peptide), F-991, FAR-404, FE 202158, Felypressin, FGLL, Frakefamide (LEF-576) (SPD-759) (BCH-3963), FX-06, Ganirelix (Org-37462) (RS-26306), Glaspimod (SKF-107647), Glatiramer (COP-1), Glucagon, Glucosamyl muramyl tripeptide, Glutoxim (NOV-002), Glypromate, GMDP, Golotimod (SCV-07), Goralatide (BIM-32001), Goserelin (ICI-118630), GPG-NH2, GTP-200, GTP-300, H-142, Hemoparatide (PTH(1-37)), Hexapeptide copper II (PC-1358), Histrelin, hLF(1-11), HP-228, I-040302 (KUR-112), Icatibant (JE-049) (HOE-140), lcrocaptide (ITF-1697), IMX-942, lpamorelin (NNC-26-0161), IPP-201101, Iseganan (IB-367), ISF402, Iturelix (ORF-23541), JTP-2942, KAI-1455, KAI-1678, KM-9803, KP-101 (GHRP-1), L-346670, L-364343, Labradimil (RMP-7), Lagatide (BN-52080), Lanreotide (ITM-014), Larazotide (AT-1001) (SPD-550), Leconotide (AM-336), Leuprolide (SOT-375), Linaclotide (MD-1100) (MM-41775), Liraglutide (NN-2211), Lixisenatide (AVE-0010) (ZP-10), LSI-518P, Lucinactant, Lusupultide (BY-2001), LY-2189265, LY-2510924, LY-548806, LYN-001, Lypressin, MER-104, Met-enkephalin (INNO-105), Metkephamide (LY-127623), Mifamurtide (CGP-19835) (MLV-19835), Montirelin (CG-3703), MPL-TLB100, MS peptide, MT-11 (PT-14), Murabutide (VA-101) (CY-220), Muramyl tripeptide, Nafarelin (RS-94991), NBI-6024, Nemifitide (INN-00835), Neogen, Nepadutant (MEN-11420), Nesiritide, Nifalatide (BW942C), NNZ-2566, NP-213, NFC-567, NPY (24-36) (PTL-041120), NT-13, Obinepitide (TM-30338), Octreotide (SMS-201-995), Oglufanide (IM-862), OGP 10-14 L, Omiganan (CPI-226), OP-145, ORG-2766 Org-42982 (AG-4263), Ornithine vasopressin, Oxytocin, Ozarelix (D-63153) (SPI-153), p-1025, P-113 (PAC-113), Pasireotide (SOM-230), peg-TPOmp (RWJ-800088), Pentigetide(TA-521), Pep-F (5K), Peptide renin inhibitor, Peptide T (AIDS000530), Peptide YY 3-36, Pexiganan (MSI-78), PF-4603629, PI-0824, PI-2301, PL-3994, PLD-116, PMX-53, POL-6326, Posatirelin, PPI-1019, Pralmorelin, Pramlintide, Protirelin, PTH (7-34), PTHrP-(1-36), PTL-0901, PXL-01, R-1516, R-15-K, R-7089, RA peptide, Ramorelix (Hoe-013), RC-3095, Re-188-P-2045 (P2045), rGRF, Romiplostim (AMG-531), Romurtide (DJ-7041), ROSE-010 (GTP-010) (LY-307161), Rotigaptide (ZP-123) (GAP-486), Rusalatide (TP-508), SAN-134, Saralasin (P-113), Secretin (human) (PGN-52) (R-52), Secretin (human) (RG-1068), Semaglutide (NN-9535), SGS-111 Sifuvirtide, SKF-101926, SKF-105494, SKF-110679 (U-75799E), Soblidotin (YHI-501) (TZT-1027), Somatostatin, Somatostatin (D-Trp, D-Cys analog), SP-304 (Guanilib), SPC-3, SPI-1620, SST analog, SUN-11031, SUN-E7001 (CS-872), SYN-1002, Tabilautide (RP-56142), TAK-448, TAK-683, Taltirelin (TA-0910), Tasidotin (ILX-651) (BSF-223651), Taspoglutide (BIM-51077), TCMP-80, Teduglutide(ALX-0600), Teriparatide (LY-333334), Terlakiren (CP-80794), Terlipressin, Tesamorelin (TH-9507), Teverelix (EP-24332), TH-0318, TH-9506, Thymalfasin, Thymodepressin, Thymonoctan (FCE-25388), Thymopentin (TP-5), Thymosin beta-4, Tifuvirtide (R-724) (T-1249), Tigapotide (PCK-3145), Tiplimotide (NBI-5788), TKS-1225 (Oxyntomodulin), TLN-232 (CAP-232)(TT-232), TM-30339, TP-9201, TRI-1144, Tridecactide (AP-214), Triletide (Z-420) (ZAMI-420), Triptorelin (WY-42462), TT-223 (E1-INT), TT-235, TX14(A), Tyroserleutide (CMS-024), Tyroservatide (CMS-024-02), Ularitide (CDD-95-126) (ESP-305), Unacylated ghrelin (AZP-01) (TH-0332), Urocortin 11, Vapreotide (RC-160), Vasopressin, VIR-576, Xen-2174, XG-102, XOMA-629, Ziconotide (SNX-111), ZP-120, or ZP-1846.

In certain embodiments, compounds of Formula (V) are selected from the group consisting of aza-analogues of AC-2592, AC-625, Anaritide, APL-180, Atriopeptin, BGC-728, Carperitide (SUN-4936), CD-NP, CG-77X56, D-4F (APP-018), Danegaptide (ZP-1609) (WAY-261134) (GAP-134), DMP-728 (DU-728), Efegatran (LY-294468), EMD-73495, Eptifibatide (C68-22), ET-642 (RLT-peptide), FE 202158, FX-06, Icatibant (JE-049) (HOE-140), lcrocaptide (ITF-1697), KAI-1455, KM-9803, L-346670, L-364343, LSI-518P, Nesiritide, Peptide renin inhibitor, PL-3994, Rotigaptide (ZP-123) (GAP-486), Saralasin (P-113), SKF-105494, Terlakiren (CP-80794), Tridecactide (AP-214), Ularitide (CDD-95-126) (ESP-305), Urocortin 11, Ziconotide (SNX-111), or ZP-120; and have utility in the treatment of cardiovascular diseases (e.g., alleviate one or more symptom(s) of a cardiovascular disease).

In certain embodiments, compounds of Formula (V) are selected from the group consisting of aza-analogues of Azetirelin (YM-14673), Conantokin G, Corticorelin (NEU-3002), CTS-21166 (ASP-1702) (ATG-Z1) (OM-00-3) (OM-99-2), Davunetide (AL-108) (AL-208), Deltibant (CP-0127), Ebiratide (Hoe-427), FGLL, Glypromate, JTP-2942, Montirelin (CG-3703), Nemifitide (INN-00835), NNZ-2566, NT-13, ORG-2766, Peptide T (AIDS000530), Posatirelin, PPI-1019, Protirelin, Secretin (human) (RG-1068), SGS-111, Taltirelin (TA-0910), XG-102, or Ziconotide (SNX-111), and have utility in the treatment of CNS disorders (e.g., alleviate one or more symptom(s) of a CNS disorder).

In certain embodiments, compounds of Formula (V) and are selected from the group consisting of aza-analogues of A-6, Abarelix (PPI-149), ABT-510, ADH-1, AEZS-108 (AN-152) (ZEN-008), Ambamustine (PTT-119), Antagonist G (PTL-68001), ATN-161, Avorelin (EP-23904), Buserelin, Carfilzomib (PR-171), CBP-501, Cemadotin (LU-103793), Chlorotoxin (TM-601), Cilengitide (EMD-121974) (EMD-85189), CTCE-9908, CVX-045, CVX-060, Degarelix (FE 200486), Didemnin B (NSC-325319), DRF-7295, Edotreotide (SMT-487), Elisidepsin (PM-02734), EP-100, Glutoxim (NOV-002), Goralatide (BIM-32001), Goserelin (ICI-118630), Histrelin, Labradimil (RMP-7), Leuprolide (SOT-375), LY-2510924, Met-enkephalin (INNO-105), Mifamurtide (CGP-19835) (MLV-19835), Muramyl tripeptide, Ozarelix (D-63153) (SPI-153), POL-6326, Ramorelix (Hoe-013), RC-3095, Re-188-P-2045 (P2045), Romurtide (DJ-7041), Soblidotin (YHI-501) (TZT-1027), SPI-1620, Tabilautide (RP-56142), TAK-448, TAK-683, Tasidotin (ILX-651) (BSF-223651), Teverelix (EP-24332), Tigapotide (PCK-3145), TLN-232 (CAP-232)(TT-232), Triptorelin (WY-42462), Tyroserleutide (CMS-024), Tyroservatide (CMS-024-02), ZP-1848, in ZT0131; and have utility in the treatment of oncological conditions (e.g., alleviate one or more symptom(s) of an oncological condition).

In certain embodiments, compounds of Formula (V) are selected from the group consisting of aza-analogues of A-623 (AMG-623), AG-284, AI-502, Allotrap 2702 (B-2702), AZD-2315, Cnsnqic-Cyclic (802-2), Delmitide (RDP-58), Dirucotide (MBP-8298) Disitertide (NAFB-001) (P-144), dnaJP1 (AT-001), Edratide (TV-4710), F-991, FAR-404, Glaspimod (SKF-107647), Glatiramer (COP-1), GMDP, IPP-201101, Icatibant (JE 049)(HOE-140), MS peptide, Org-42982 (AG-4263), Pentigetide(TA-521), PI-0824, PI-2301, PLD-116, PMX-53, PTL-0901, RA peptide, TCMP-80, Thymodepressin, Thymopentin (TP-5), Tiplimotide (NBI-5788), or ZP-1848; and have utility in the treatment of allergy and immunology disorders.

In certain embodiments, compounds of Formula (V) are selected from the group consisting of aza-analogues of A-71378, AC-162352 (PYY 3-36), AC-253, AG2/102, AKL-0707 (LAB GHRH), Albiglutide (GSK-716155), AOD-9604, BAY-73-7977, BIM-44002, BMS-686117, BRX-0585, CJC-1131 (DAC:GLP-1), CJC-1134 (PC-DAC)

(Exendin-4), CJC-1295 (DAC:GRF), CP-95253, CVX-096 (PF-4856883), Davalintide (AC-2307), Exenatide (AC-2993) (LY-2148568), Exsulin (INGAP Peptide), Glucagon, ISF402, Liraglutide (NN-2211), Lixisenatide (AVE-0010) (ZP-10), LY-2189265, LY-548806, nafarelin (RS 94991), NBI-6024, Obinepitide (TM-30338), Peptide YY 3-36, PF-4603629, Pramlintide, R-7089, Semaglutide (NN-9535), SST analog, SUN-E7001 (CS-872), Taspoglutide (BIM-51077), Tesamorelin (TH-9507), TH-0318, TKS-1225 (Oxyntomodulin), TM-30339, TT-223 (E1-INT), Unacylated ghrelin (AZP-01) (TH-0332), or ZT0131, and have utility in the treatment of metabolic disorders (e.g., alleviate one or more symptom(s) of a metabolic disorder).

In certain embodiments, compounds of Formula (V) are selected from the group consisting of aza-analogues of A-75998, Buserelin, Cetrorelix (NS-75), Detirelix (RS-68439), Ganirelix (Org-37462) (RS-26306), Iturelix, Nafarelin (RS-94991), or triproletin (WY-42462); and have utility in the treatment of fertility.

In certain embodiments, compounds of Formula (V) are selected from the group consisting of aza-analogues of AC-100 and p-1025, and have utility in the treatment of dental disorders.

In certain embodiments, compounds of Formula (V) are selected from the group consisting of aza-analogues of ACV-1, Conantokin G, CJC-1008 (DAC: Dynorphin A), Contulakin G (CGX-1007), CR-665, CR-845, Dynorphin A, E-2078, Felypressin, Frakefamide (LEF-576) (SPD-759) (BCH-3963), HP-228, Icatibant (JE-049) (HOE-140), KAI-1678, Leconotide (AM-336), Metkephamide (LY-127623), MPL-TLB100, NT-13, SYN-1002, TX14(A), Xen-2174, and Ziconotide (SNX-111); and have utility in the treatment of pain.

In certain embodiments, compounds of Formula (V) are selected from the group consisting of aza-analogues of Afamelanotide (EP-1647) (CUV-1647) (Melanotan I), AZX-100, DPK-060, DSC-127, Hemoparatide (PTH(1-37)), Hexapeptide copper II (PC-1358), Pexiganan (MSI-78), PTH (7-34), PXL-01, SKF-110679 (U-75799E), or Thymosin beta-4; and have utility in the treatment of dermatologic conditions (e.g., alleviate one or more symptom(s) of a dermatologic condition).

In certain embodiments, compounds of Formula (V) are selected from the group consisting of aza-analogues of AF-37702, Bivalirudin (BG-8865), carfilzomib, (PR-171), CTCE-0214, ETRX 101, H-142, OGP 10-14 L, Ornithine vasopressin, peg-TPOmp (RWJ-800088), R-1516, Romiplostim (AMG-531), and TP-9201; and have utility in the treatment of hematology disorders (e.g., alleviate one or more symptom(s) of a hematology disorder).

In certain embodiments, compounds of Formula (V) are selected from the group consisting of aza-analogues of Albuvirtide, ALG-889, Alloferon, ALX-40-4C, CB-182804, CB-183315, CZEN-002, Enfuvirtide (T-20), Glucosamyl muramyl tripeptide, Golotimod (SCV-07), GPG-NH2, hLF (1-11), IMX-942, Iseganan (IB-367), Murabutide (VA-101) (CY-220), Neogen, NP-213, Oglufanide (IM-862), Omiganan (CPI-226), OP-145, p-1025, P-113 (PAC-113), Pep-F (5K), R-15-K, Sifuvirtide, SPC-3, Thymalfasin, Thymonoctan (FCE-25388), Tifuvirtide (R-724) (T-1249), TRI-1144, VIR-576, or XOMA-629; and have utility as an antimicrobial or antiviral agent.

In certain embodiments, compounds of Formula (V) are selected from the group consisting of aza-analogues of ALTY-0601, B27PD, BDM-E, BIM-23190, CBT-101, Compstatin (POT-4), Eledoisin (ELD-950), and LYN-001, and have utility in the treatment of ophthalmologic disorders.

In certain embodiments, compounds of Formula (V) are selected from the group consisting of aza-analogues of Atosiban (ORF-22164), Barusiban (FE-200400), Carbetocin, Cargutocin (Y-5350), Deslorelin, Oxytocin, or TT-235, and have utility in the treatment of OB-GYN disorders.

In certain embodiments, compounds of Formula (V) are selected from the group consisting of aza-analogues of Aviptadil (PSD-510), Bremelanotide (PT-141), C-peptide (SPM-933), Desmopressin, EA-230, Lypressin, MER-104, MT-11 (PT-14), SKF-101926, or Vasopressin, and have utility in the treatment of urologic conditions (e.g., alleviate one or more symptom(s) of a urologic condition).

In certain embodiments, compounds of Formula (V) are selected from the group consisting of aza-analogues of AC-100, BA-058, Calcitonin (Human), Calcitonin (Salmon), Elcatonin, I-040302 (KUR-112), PTHrP-(1-36), Rusalatide (TP-508), SAN-134, Teriparatide (LY-333334), or ZT031; and have utility in the treatment of bones and connective tissue disorders.

In certain embodiments, compounds of Formula (V) are selected from the group consisting of aza-analogues of BIO-1211, CGRP (LAB-CGRP), Glucosamyl muramyl tripeptide, GMDP, Icrocaptide (ITF-1697), Lucinactant, Lusupultide (BY-2001), NPC-567, NPY (24-36) (PTL-041120), or Secretin (human) (PGN-52) (R-52); and have utility in the treatment of respiratory conditions (e.g., alleviate one or more symptom(s) of a respiratory condition).

In certain embodiments, compounds of Formula (V) are selected from the group consisting of aza-analogues of Casokefamide, CCK (25-33), Lagatide (BN-52080), Larazotide (AT-1001) (SPD-550), Linaclotide (MD-1100) (MM-41775), Nepadutant (MEN-11420), Nifalatide (BW942C), ROSE-010 (GTP-010) (LY-307161), Somatostatin, Somatostatin (D-Trp, D-Cys analog), SP-304 (Guanilib), Teduglutide(ALX-0600), Terlipressin, Triletide (Z-420) (ZAMI-420), Vapreotide (RC-160), ZP-1846, or ZP-1846; and have utility in the treatment of gastroenterologic disorders (e.g., alleviate one or more symptom(s) of a gastroenterologic disorder).

In certain embodiments, compounds of Formula (V) are selected from the group consisting of aza-analogues of CJC-1295 (DAC:GRF), DG-3173 (PTR-3173), Dopastatin (BIM-23A760), EP-51216 (EP-51389), Examorelin (EP-23905) (MF-6003), GTP-200 (GTP-300), lpamorelin (NNC-26-0161), Iturelix (ORF-23541), KP-101 (GHRP-1), Lanreotide (ITM-014), Octreotide (SMS-201-995), Pasireotide (SOM-230), Pralmorelin, rGRF, SUN-11031, TH-9506, ZT0131, or vapreotide (RC-160); and have utility in the treatment of endocrinology disorders (e.g., alleviate one or more symptom(s) of a gastroenterologic disorder).

Example 1

S-ethyl 2-((((9H-fluoren-9-yl)methoxy)carbonyl)glycyl)-1-benzylhydrazine-1-carbothioate: [FmocGlyAzaPhe(SEt) (A11120)]

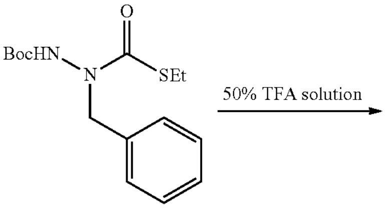

1

-continued

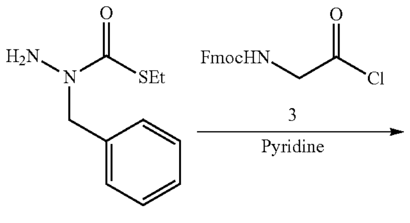

2

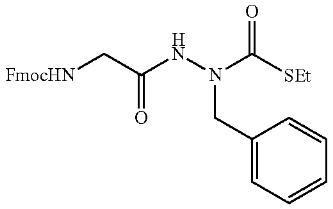

Chemical Formula: $C_{27}H_{27}N_3O_4S$
Exact Mass: 489.17
A11120

To a solution of thiocarbazate 1 (880 mg, 2.8 mmol) in DCM (5.0 mL), was added at 0° C. TFA (5.0 mL). The reaction mixture was warmed up gradually to room temperature and stirred for an additional 30 min. After disappearing the starting material based on TLC, all volatiles were evaporated under vacuum to give the deprotected thiocarbazate 2, which was used directly in the next step without further purification. Thiocarbazate 2 (based on 2.8 mmol) was dissolved in THF (10 mL) and then treated with pyridine (232 uL, 2.94 mmol). The reaction mixture was stirred at 0° C., then a solution of the FmocGly(Cl) 3 (894 mg, 2.8 mmol) in THF (5.0 mL) was added slowly using a syringe pump with the rate of 10 mL/h. Upon completion of the addition, the reaction was stirred at room temperature for an additional hour; then, it was stopped by adding a saturated solution of $NH_4Cl$. The aqueous layer was extracted with EtOAc (10 mL×3), and the combined organic layers were dried over $Na_2SO_4$, filtered, and evaporated under vacuum. The crude material was purified over silica using the Combi Flash® machine and the using gradient mobile phase of EtOAc/hexanes to give 1100 mg of the titled product A11120 (80% yield). Representative structures were confirmed by $^1$HNMR and $^{13}$CNMR. $^1$HNMR for the major isomer (500 MHz, DMSO-$d_6$) δ 10.59 (s, 1H), 7.94 (d, J=7.55 Hz, 2H), 7.77 (d, J=7.45 Hz, 2H), 7.72 (t, J=6.05 Hz, 1H), 7.47 (t, J=7.4 Hz, 2H), 7.39-7.29 (m, 7H), 5.23 (d, J=14.3 Hz, 1H), 4.35-4.24 (m, 3H), 4.07 (m, 1H), 3.68 (m, 2H), 2.78 (q, J=7.14, 14.4 Hz, 2H), 1.20 (t, J=7.4 Hz, 3H). $^{13}$CNMR (125 MHz, DMSO$d_6$) δ 171.7, 169.9, 157.4, 144.8, 141.7, 137.2, 129.5, 129.4, 129.3, 128.6, 128.5, 128.1, 126.3, 121.1, 66.8, 60.76, 52.8, 47.7, 42.8, 24.7, 16.1. LRMS m/z calculated for $C_{27}H_{28}N_3O_4S$ [M+H] 490.18 found 490.20.

Example 2 tert-butyl 2-(2-benzyl-2-((ethylthio)carbonyl)hydrazine-1-carbonyl)pyrrolidine-1-carboxylate: [BocProAzaPhe(SEt) (A9065-2)]

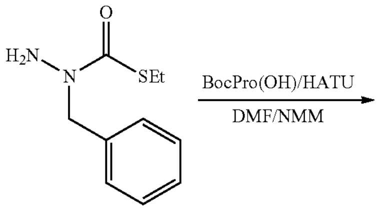

2

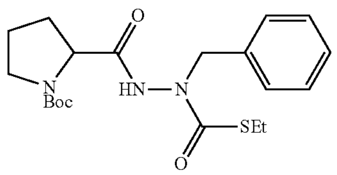

Chemical Formula: $C_{20}H_{29}N_3O_4S$
Exact Mass: 407.9
A90065-2

To a solution of thiocarbazate 2 (304 mg, 1.45 mmol) in DMF (8.0 mL) was added N-Boc Proline (343 mg, 1.59 mmol), HATU (722.4 mg, 1.59 mmol), HOBt (214 mg, 1.59 mmol), and M-methyl morpholine (650 uL, 6.4 mmol). The reaction mixture was stirred at room temperature for 20 hours, then was treated with 0.5 M citric acid solution. The aqueous layer was extracted with EtOAc (15.0 mL×3), the combined organic fractions were washed with saturated sodium bicarbonates solution, brine, and cold water. The organic layer was dried over sodium sulfate, filtered, and evaporated to dryness. The crude material was purified on silica using Combi Flash Machine® and gradient EtOAc/Hexanes. The collected product weighs 248 mg, (42% yield). LRMS (ESI, MNa+) m/z calc for $C_{20}H_{29}N_3O_4SNa$+ 430.18, found 430.3.

Example 3

(9H-fluoren-9-yl)methyl 2-(2-benzyl-2-((ethylthio)carbonyl)hydrazine-1-carbonyl)pyrrolidine-1-carboxylate: [FmocProAzaPhe(SEt) (A11123)]

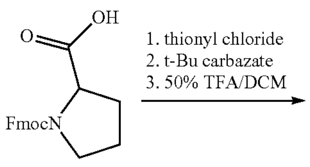

3

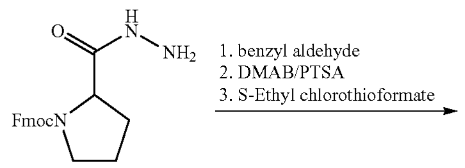

4

-continued

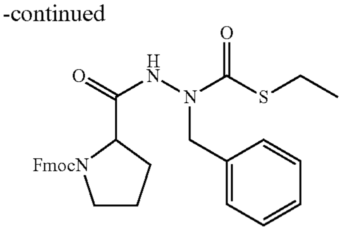

Chemical Formula: $C_{30}H_{31}N_3O_4S$
Exact Mass: 529.20
A11123

To a solution of Fmoc proline 3 (5.0 g, 14.8 mmol) in DCM (50 mL) was added DMF (50 uL) and thionyl chloride (5.0 mL). The reaction mixture was stirred at 0° C. for 30 min then was stirred at room temperature for another 30 min. Later, the excess solvents were removed under vacuum, and the crude material was dried further under high vacuum for one hour and used in the next step without purification.

To a solution of t-Bu carbazate (2.0 g, 14.8 mmol) in THF (30 mL) was added Pyridine (1.2 mL, 14.8 mmol). The reaction was stirred at 0° C. for 5 min, then was treated with Fmoc Pro (Cl) solution from the previous step (14.8 mmol/5.0 mL THF); the Fmoc Pro (Cl) was added dropwise using a syringe pump at a rate of 10 mL/h. The reaction was stopped after one hour by adding 20 mL of saturated ammonium chloride; the aqueous layer was transferred to a separatory funnel and extracted with EtOAc (20 mL×3). The combined organic layer was washed with water (20 mL×3), dried over sodium sulfate, filtered, and evaporated to dryness. The crude material was eluted quickly through a silica gel pad to remove the unreacted t-Bu carbazate and the Fmoc Proline amino acid. Half of the resulting semicarbazate (7.4 mmol) was dissolved in DCM (5.0 mL) and treated at 0° C. with TFA (5.0 mL). The reaction mixture was stirred at 0° C. and warmed up gradually for 30 min. Later the excess solvent was removed under vacuum, and the resulting material was dissolved in DCM (5.0 mL) and THE (10.0 mL). To the reaction mixture was added benzaldehyde (1.0 mL, ten mmol) and anhydrous $MgSO_4$ (2.0 g). The reaction mixture was heated to reflux and stirred at 60° C. for 30 min; then it was filtered over a celite pad; the filtrate was evaporated to dryness and redissolved in DCM (20 mL). The reaction mixture was placed in an ice/acetone bath (−6° C.) and treated with $BH_3{\cdot}NMe_2$ (928 mg, 16 mmol) and PTSA (11.5 g, 60 mmol). The PTSA was dissolved in a 3:1 ratio of DCM/MeOH (18 mL) and introduced slowly in a portion-wise manner. The reaction was stopped after 30 min by adding slowly at 0° C. 10% $Na_2CO_3$ solution (50 mL). When the gas completely ceased off. The mixture was heated to reflux for another 30 min at 60° C. The aqueous layer was extracted with DCM (20 mL×3). The organic layer was washed A11123 successively with brine and water, dried over $Na_2SO_4$, filtered, and evaporated to dryness. The crude material was purified over silica, and gradient of EtOAc/Hexane, the resulting substituted hydrazine (2.6 g, 5.0 mmol) was dissolved in THF (10 mmol) and treated with Pyridine (442 uL, 5.6 mmol) and 0.5 M solution of S-ethylchlorothioformate in DCM (12 mL, 6 mmol). The reaction mixture was stirred at 0° C. for 30 min; then, it was transferred to a separatory funnel. The organic layer was washed with water, dried over $Na_2SO_4$, filtered, and evaporated. The crude material was purified over silica using Combi Flash Machine® and a gradient solvent EtOAc/Hexane to give the tilted compound A11123 (1.8 g, 34% over 6 steps). Representative structures were confirmed by $^1$HNMR and $^{13}$CNMR. $^1$HNMR for the major isomer (500 MHz, DMSO-d6) δ 10.67 (s, 1H), 7.91 (m, 2H), 7.68 (m, 2H), 7.54-7.09 (m, 9H), 5.15 (m, 1H), 4.44-3.98 (m, 4H), 3.64-3.34 (m, 2H), 2.77 (m, 2H), 2.14-1.76 (m, 4H), 1.18 (t, J=7.3 Hz, 3H). $^{13}$CNMR (125 MHz, DMSOd6) for the major isomer δ 172.1, 154.7, 144.8, 141.7, 141.6, 141.5, 137.0, 130.0, 129.4, 129.3, 128.6, 128.5, 128.3, 126.5, 126.3, 121.1, 67.6, 58.9, 52.8, 47.5, 47.3, 31.9, 30.0, 24.7, 21.7, 16.1. LRMS m/z calculated for $C_{30}H_{32}N_3O_4S$ [M+H] 530.21 found 530.25.

Example 4

S-ethyl 2-((((9H-fluoren-9-yl)methoxy)carbonyl)-L-phenylalanyl)-1-(3-((tert-butoxycarbonyl)amino) propyl)hydrazine-1-carbothioate: [FmocPheAzaOrn (SEt) (A11124)]

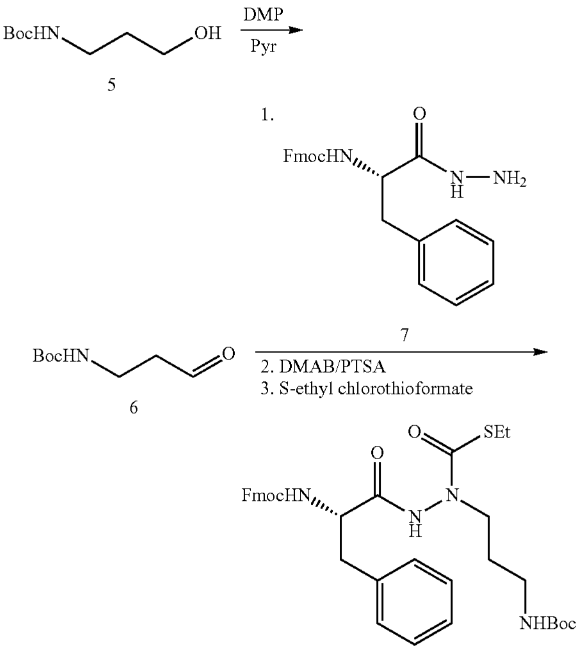

Chemical Formula: $C_{35}H_{42}N_4O_8S$
Exact Mass: 646.28
A11124

To a solution of alcohol 5 (1.7 g, 10 mmol) in DCM (30 mL) was added pyridine (4.7 mL, 60 mmol) and DMP (4.2 g, 10 mmol). The reaction mixture was stirred at room temperature for one hour; then, the DCM was concentrated under vacuum at room temperature. The resulting crude mixture was dissolved in diethyl ether (50 mL) and treated with 2 M NaOH solution. The organic layer was washed with brine, water, dried over $Na_2SO_4$, filtered, and evaporated to dryness. The resulting aldehyde was used in the next step without further purification. To a solution of aldehyde 6 (10.0 mmol) in DCM (5.0 mL) and THF (5.0 mL) was added hydrazine 7 (1300 mg, 3.0 mmol) and $MgSO_4$ (1.0 g). The reaction mixture was heated to reflux at 60° C. for 30 min, then it was filtered over celite pad. The filtrate was concentrated under vacuum and redissolved in DCM (20.0 mL). The solution was placed in an ice bath and treated with $BH_3{\cdot}Me_2$ (460 mg, 8.0 mmol) and PTSA (3.8 g, 20.0 mmol). The PTSA was dissolved in a 3:1 ratio of DCM/MeOH (18 mL) and introduced slowly in a portion-wise manner. The reaction was stopped after 30 min by adding slowly at 0° C. 10% $Na_2CO_3$ solution (50 mL). When the gas completely ceased off. The mixture was heated to reflux (40° C.) for another 30 min at 60° C. The aqueous layer was extracted with DCM (20 mL×3). The organic layer was washed successively with brine and water, dried over $Na_2SO_4$, filtered, and evaporated to dryness. The crude material was purified over silica gel, and gradient of EtOAc/Hexane. The resulting substituted hydrazine (3.0 mmol) was dissolved in THF (10 mmol) and treated with Pyridine (237 uL, 3.0 mmol) and 0.5 M solution of S-ethylchlorothioformate in DCM (6.0 mL, 3 mmol). The reaction mixture was stirred at 0° C. for 30 min; then, it was transferred to a separatory funnel. The organic layer was washed with water, dried over $Na_2SO_4$, filtered, and evaporated. The crude material was purified over silica using Combi Flash Machine® and a gradient solvent EtOAc/Hexane to give the titled compound A11124 (1.1 g, 17% over 6 steps). LRMS m/z calculated for $C_{35}H_{42}N_4O_6SNa$ [M+Na] 669.27 found 669.33.

Example 5

S-ethyl 2-((((9H-fluoren-9-yl)methoxy)carbonyl)-L-phenylalanyl)-1-benzylhydrazine-1-carbothioate: [FmocPheAzaPhe(SEt) (A11125)]

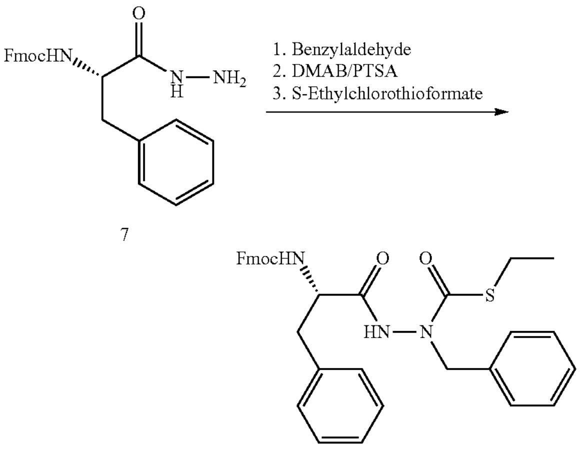

7

Chemical Formula: $C_{34}H_{33}N_3O_4S$
Exact Mass: 579.22
A11125

To a solution of Hydrazine 7 (1.2 g, 3.0 mmol) in DCM (10 mL) and THF (20.0 mL) was added Benzylaldehyde (320 uL, 3.0 mmol) and $MgSO_4$ (2 g). The reaction mixture was refluxed for 30 min at 60° C., then it was filtered over celite pad. The filtrate was concentrated under vacuum and redissolved in DCM (10.0 mL). The solution was placed in an ice bath and treated with $BH_3 \cdot Me_2$ (278 mg, 4.8 mmol) and PTSA (2.9 g, 15 mmol). The PTSA was dissolved in a 3:1 ratio of DCM/MeOH (9.0 mL) and introduced slowly in a portion-wise manner. The reaction was stopped after 30 min by adding slowly at 0° C. 10% $Na_2CO_3$ solution (50 mL). When the gas completely ceased off, the mixture was heated to reflux (40° C.) for another 30 min at 60° C. The aqueous layer was extracted with DCM (20 mL×3). The organic layer was washed successively with brine and water, dried over $Na_2SO_4$, filtered, and evaporated to dryness. The crude material was purified over silica gel, and gradient of EtOAc/Hexane, the resulting substituted hydrazine (3.0 mmol) was dissolved in THF (10 mmol) and treated with Pyridine (237 uL, 3.0 mmol) and 0.5 M solution of S-ethylchlorothioformate in DCM (6.0 mL, 3 mmol). The reaction mixture was stirred at 0° C. for 30 min; then, it was transferred to a separatory funnel. The organic layer was washed with water, dried over $Na_2SO_4$, filtered, and evaporated. The crude material A11125 was purified over silica using Combi Flash Machine® and a gradient solvent EtOAc/Hexane to give the tilted compound A11125 (100 mg, 5.7% over 3 steps). Representative structures were confirmed by $^1$HNMR and $^{13}$CNMR. $^1$HNMR for the major isomer (500 MHz, DMSO-d6) δ 10.81 (s, 1H), 7.86 (m, 3H), 7.65 (m, 2H), 7.34-7.20 (m, 13H), 5.26 (m, 1H), 4.28 (m, 1H), 4.17 (m, 3H), 4.02 (m, 1H), 3.12 (m, 1H), 2.78 (m, 3H), 1.18 (m, 3H). $^{13}$CNMR (125 MHz, DMSOd6) for the major isomer δ 172.3, 172.6, 156.9, 144.6, 141.6, 138.8, 137.1, 130.2, 129.5, 129.4, 129.2, 129.1, 128.6, 128.0, 127.4, 126.3, 126.2, 121.1, 66.6, 60.7, 55.9, 52.7, 47.5, 24.7, 16.1. LRMS m/z calculated for $C_{34}H_{34}N_3O_4S$ [M+H] 580.23 found 580.33.

Example 6

S-ethyl (S)-2-(2-((((9H-fluoren-9-yl)methoxy)carbonyl)amino)-3-(4-(tert-butoxy)phenyl)propanoyl) pyrazolidine-1-carbothioate: [FmocTyrAzaPro(SEt) (A11143)]

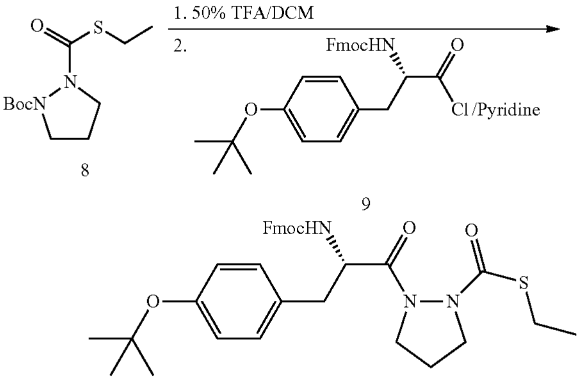

Chemical Formula: $C_{34}H_{39}N_3O_5S$
Exact Mass: 601.26
A11143

To a solution of thiocarbazate 8 (880 mg, 3.4 mmol) in DCM (10.0 mL), was added at 0° C. TFA (10.0 mL). The reaction mixture was warmed up gradually to room temperature and stirred for an additional 30 min. After the disappearing of the starting material based on TLC, all volatiles were removed under vacuum to give the deprotected thiocarbazate, which was used directly in the next step without further purification. The resulting thiocarbazate (based on 3.4 mmol) was dissolved in THF (10 mL) and then treated with pyridine (395 uL, 5.0 mmol). The reaction mixture was stirred at 0° C., then a solution of the FmocTyr (Cl) 9 (2.38 g, 5.0 mmol) in THF (5.0 mL) was added slowly using a syringe pump pro with the rate of 10 mL/h. Upon completion of the addition, the reaction was stirred at room temperature for an additional hour; then, it was stopped by adding a saturated solution of $NH_4Cl$. The aqueous layer was extracted with EtOAc (10 mL×3), and the combined organic layers were dried over $Na_2SO_4$, filtered, and evaporated under vacuum. The crude material was purified over silica using the Combi Flash® machine and the using gradient mobile phase of EtOAc/hexanes to give 1.05 mg of the titled product A11143 (51% yield). LRMS m/z calculated for $C_{34}H_{39}N_3O_5SNa$ [M+Na] 624.25 found 624.42.

Example 7

BocProPhePhe(StBu) was prepared by solution phase synthesis utilizing BocProPhe(SeEt). The following synthetic scheme was used

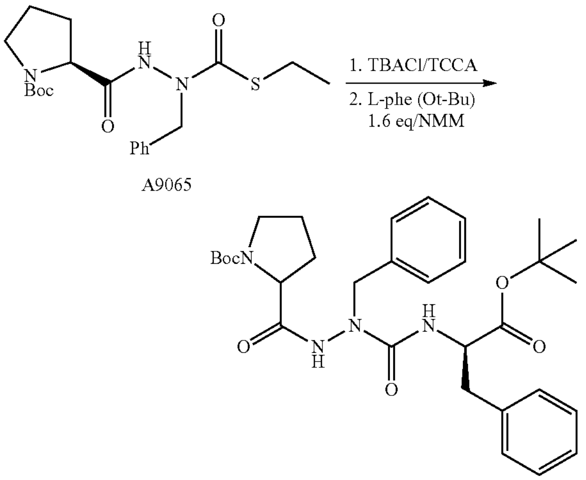

A9065

Chemical Formula: $C_{31}H_{42}N_4O_6$
Exact Mass; 566.31
A11133

To a solution of A9065 (41 mg, 0.1 mmol) in DCM (0.5 mL) was added TBACl (28 mg, 0.1 mmol) and TCCA (23 mg, 0.1 mmol). The reaction was stirred at room temperature vigorously for 5 min; then, it was treated with t-butyl phenylalanine ester (39 mg, 0.15 mmol) and Et3N (55 uL, 0.4 mmol). Then, the reaction mixture was stirred at room temperature for an additional hour. The reaction mixture was diluted with EtOAc (2.5 mL) and transferred into a separatory funnel. The organic layer was washed with ammonium chloride and brine, dried over sodium sulfate, filtered, and evaporated under vacuum. The crude mixture was analyzed by TLC and mass spectrometry.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense. All documents cited herein, as well as text appearing in the FIGURES, are hereby incorporated by reference in their entirety for all purposes to the same extent as if each were so individually denoted.

What is claimed is:

1. A compound of Formula (I):

(I)

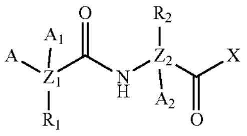

and salts thereof, wherein

A is N-phthalimidyl or $NR_3R_4$, wherein (i) $R_3$ is H and $R_4$ is 9-fluorenylmethoxycarbonyl or 2-(3,5-dimethoxyphenyl) propan-2-yloxycarbonyl or (ii) $R_3$ and $R_1$ are connected and together form a side chain radical of proline and $R_4$ is tert-butoxycarbonyl, 9-fluorenylmethoxycarbonyl or 2-(3,5-dimethoxyphenyl) propan-2-yloxycarbonyl;

$A_1$ is H or absent;

$A_2$ is H or absent;

X is selected from the group consisting of imidazolyl, benzotriazolyl, S-D, and O-L;

D is H, Cl, an alkyl, an aryl or a heteroaryl;

L is imidazolyl or benzotriazolyl;

$R_1$ and $R_2$ is each independently selected from the group consisting of side chain radicals of amino acids selected from the group consisting of side chain radicals of aspartic acid, phenylalanine, alanine, histidine, glutamic acid, tryptophan, valine, leucine, lysine, methionine, threonine, tyrosine, isoleucine, arginine, glycine, asparagine, serine, and glutamine;

$Z_1$ and $Z_2$ is each independently C or N; and at least one of $Z_1$ and $Z_2$ is N.

2. A compound of Formula (I):

(I)

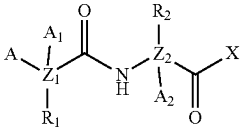

and salts thereof, wherein

A is $NR_3R_4$, wherein (i) $R_3$ is H and $R_4$ is 9-fluorenylmethoxycarbonyl or 2-(3,5-dimethoxyphenyl) propan-2-yloxycarbonyl or (ii) $R_3$ and $R_1$ are connected and together form a side chain radical of proline and $R_4$ is tert-butoxycarbonyl, 9-fluorenylmethoxycarbonyl or 2-(3,5-dimethoxyphenyl) propan-2-yloxycarbonyl;

$A_1$ is H or absent;

$A_2$ is H or absent;

X is selected from the group consisting of imidazolyl, benzotriazolyl, S-D, and O-L;

D is H, Cl, an alkyl, an aryl or a heteroaryl;

L is imidazolyl or benzotriazolyl;

$R_1$ and $R_2$ is each independently selected from the group consisting of side chain radicals of amino acids selected from the group consisting of side chain radicals of aspartic acid, phenylalanine, alanine, histidine, glutamic acid, tryptophan, valine, leucine, lysine, methionine, threonine, tyrosine, isoleucine, arginine, glycine, asparagine, serine, and glutamine; and $Z_1$ is N and $Z_2$ is C, or $Z_1$ is C and $Z_2$ is N.

3. A compound according to claim 1, wherein A is $NR_3R_4$, wherein $R_3$ is H and $R_4$ is 9-fluorenylmethoxycarbonyl or 2-(3,5-dimethoxyphenyl) propan-2-yloxycarbonyl.

4. A compound according to claim 1, wherein A is N-phthalimidyl.

5. A compound according to claim 1, wherein A is $NR_3R_4$, $R_3$ is H, $R_4$ is 9-fluorenylmethoxycarbonyl or 2-(3,5-dimethoxyphenyl) propan-2-yloxycarbonyl, and $R_3$ and $R_1$ are connected and together form a side chain radical of proline.

6. A compound according to claim 1, wherein X is benzotriazolyl.

7. A compound according to claim 1, wherein X is S-D; and D is an alkyl.

8. A compound according to claim 7, wherein the alkyl is ethyl.

9. A compound according to claim 1, wherein X is selected from a group consisting of S-D and O-L.

10. A compound according to claim 2, wherein X is selected from the group consisting of S-D and O-L.

11. A compound according to claim 1, wherein $Z_1$ and $Z_2$ are both N.

12. A compound according to claim 1, wherein $Z_1$ is C, and $Z_2$ is N.

13. A compound according to claim 1 wherein the side chain radicals of amino acids are selected from the group consisting of side chain radicals of aspartic acid, phenylalanine, alanine, histidine, glutamic acid, tryptophan, valine, leucine, lysine, methionine, threonine, tyrosine, isoleucine, arginine, asparagine, serine, and glutamine.

14. A compound according to claim 2, wherein A is $NR_3R_4$, $R_3$ is H and $R_4$ is 9-fluorenylmethoxycarbonyl or 2-(3,5-dimethoxyphenyl) propan-2-yloxycarbonyl.

15. A compound according to claim 14, wherein $R_4$ is 9-fluorenylmethoxycarbonyl.

16. A compound according to claim 1, wherein X is selected from a group consisting of imidazolyl, benzotriazolyl, and S-D.

17. A compound according to claim 1, which is (9H-fluoren-9-yl)methyl 2-(2-benzyl-2-((ethylthio) carbonyl) hydrazine-1-carbonyl) pyrrolidine-1-carboxylate.

18. A compound according to claim 1, wherein

A is $NR_3R_4$, and $R_3$ and $R_1$ are connected and together form a side chain radical of proline and $R_4$ is 9-fluorenylmethoxycarbonyl;

$A_1$ is absent;

$A_2$ is absent;

$Z_1$ is C;

$Z_2$ is N;

X is S-D or O-L; and

L is an alkyl.

19. A compound according to claim 2, wherein

A is $NR_3R_4$, and $R_3$ and $R_1$ are connected and together form a side chain radical of proline and $R_4$ is 9-fluorenylmethoxycarbonyl;

$A_1$ is absent;

$A_2$ is absent;

$Z_1$ is C;

$Z_2$ is N;

X is S-D or O-L; and

L is an alkyl.

* * * * *